(12) United States Patent
Fischer et al.

(10) Patent No.: US 9,492,191 B2
(45) Date of Patent: Nov. 15, 2016

(54) TOOLS AND METHODS FOR TREATMENT OF PELVIC CONDITIONS

(75) Inventors: Brian G. Fischer, Minneapolis, MN (US); Karl A. Jagger, Deephaven, MN (US); Jason W. Ogdahl, Minneapolis, MN (US); Jeffrey M. O'Hern, Golden Valley, MN (US); John F. Otte, St. Anthony, MN (US); Jessica L. Roll, Maple Grove, MN (US); Andrew P. VanDeWeghe, St. Louis Park, MN (US); Justin H. Huelman, Lino Lakes, MN (US); Chaouki A. Khamis, Edina, MN (US)

(73) Assignee: Astora Women's Health, LLC, Eden Prairie, MN (US)

( * ) Notice: Subject to any disclaimer, the term of this patent is extended or adjusted under 35 U.S.C. 154(b) by 311 days.

(21) Appl. No.: 13/566,613

(22) Filed: Aug. 3, 2012

(65) Prior Publication Data

US 2013/0035543 A1 Feb. 7, 2013

Related U.S. Application Data

(60) Provisional application No. 61/515,160, filed on Aug. 4, 2011, provisional application No. 61/515,698, filed on Aug. 5, 2011.

(51) Int. Cl.
*A61F 2/02* (2006.01)
*A61B 17/32* (2006.01)
(Continued)

(52) U.S. Cl.
CPC ..... *A61B 17/320016* (2013.01); *A61F 2/0045* (2013.01); *A61B 17/3201* (2013.01); *A61B 17/32056* (2013.01); *A61B 2017/00805* (2013.01); *A61B 2017/32004* (2013.01)

(58) Field of Classification Search
CPC ............... A61B 17/0057; A61B 17/00234; A61B 17/320016; A61B 2017/32004; A61B 17/32056; A61B 2017/00805; A61B 17/3201; A61F 2/0036; A61F 2/0004
USPC .............. 600/29, 30, 37; 606/151, 157
See application file for complete search history.

(56) References Cited

U.S. PATENT DOCUMENTS 1,615,728 A * 1/1927 Smith ............... A61D 9/02
128/834
2,738,790 A 3/1956 Todt et al.
(Continued)

FOREIGN PATENT DOCUMENTS

AU 2002241673 11/2005
CA 2404459 8/2005
(Continued)

OTHER PUBLICATIONS

"We're staying ahead of the curve" Introducing the IVS Tunneller Device for Tension Free Procedures, Tyco Healthcare, 3 pages (2002).
(Continued)

*Primary Examiner* — Navin Natnithithadha
*Assistant Examiner* — Sunita Reddy
(74) *Attorney, Agent, or Firm* — Kagan Binder, PLLC

(57) ABSTRACT

Surgical procedures, systems, implants, devices, tools, and methods that are used for treating pelvic conditions in a male or female, the pelvic conditions including incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), and other conditions caused by muscle and ligament weakness, the devices and tools including devices and tools for anchoring an implant to tissue, adjusting the length of implant components, and cutting the implant to a desired length.

14 Claims, 23 Drawing Sheets

(51) Int. Cl.
  *A61F 2/00*      (2006.01)
  *A61B 17/3201*   (2006.01)
  *A61B 17/3205*   (2006.01)
  *A61B 17/00*     (2006.01)

(56)                References Cited

U.S. PATENT DOCUMENTS

| | | | |
|---|---|---|---|
| 3,124,136 A | 3/1964 | Usher | |
| 3,182,662 A | 5/1965 | Shirodkar | |
| 3,311,110 A | 3/1967 | Singerman et al. | |
| 3,384,073 A | 5/1968 | Van Winkle, Jr. | |
| 3,472,232 A | 10/1969 | Earl | |
| 3,580,313 A | 5/1971 | McKnight | |
| 3,763,860 A | 10/1973 | Clarke | |
| 3,789,828 A | 2/1974 | Schulte | |
| 3,815,576 A | 6/1974 | Balaban | |
| 3,858,783 A | 1/1975 | Kapitanov et al. | |
| 3,924,633 A | 12/1975 | Cook et al. | |
| 3,995,619 A | 12/1976 | Glatzer | |
| 4,019,499 A | 4/1977 | Fitzgerald | |
| 4,037,603 A | 7/1977 | Wendorff | |
| 4,128,100 A | 12/1978 | Wendorff | |
| 4,172,458 A | 10/1979 | Pereyra | |
| 4,235,238 A | 11/1980 | Ogiu et al. | |
| 4,246,660 A | 1/1981 | Wevers | |
| 4,441,497 A | 4/1984 | Paudler | |
| 4,509,516 A | 4/1985 | Richmond | |
| 4,548,202 A | 10/1985 | Duncan | |
| 4,632,100 A | 12/1986 | Somers et al. | |
| 4,775,380 A | 10/1988 | Seedhom et al. | |
| 4,857,041 A | 8/1989 | Annis et al. | |
| 4,865,031 A | 9/1989 | O'Keeffe | |
| 4,873,976 A | 10/1989 | Schreiber | |
| 4,920,986 A | 5/1990 | Biswas | |
| 4,932,962 A | 6/1990 | Yoon et al. | |
| 4,938,760 A | 7/1990 | Burton et al. | |
| 4,969,892 A | 11/1990 | Burton et al. | |
| 5,007,894 A | 4/1991 | Enhorning | |
| 5,012,822 A | 5/1991 | Schwarz | |
| 5,013,292 A | 5/1991 | Lemay | |
| 5,013,316 A | 5/1991 | Goble et al. | |
| 5,019,032 A | 5/1991 | Robertson | |
| 5,032,508 A | 7/1991 | Naughton et al. | |
| 5,036,867 A | 8/1991 | Biswas | |
| 5,053,043 A | 10/1991 | Gottesman et al. | |
| 5,085,661 A | 2/1992 | Moss | |
| 5,112,344 A | 5/1992 | Petros | |
| 5,123,428 A | 6/1992 | Schwarz | |
| 5,141,520 A | 8/1992 | Goble et al. | |
| 5,149,329 A | 9/1992 | Richardson | |
| 5,188,636 A | 2/1993 | Fedotov | |
| 5,209,756 A | 5/1993 | Seedhom et al. | |
| 5,250,033 A | 10/1993 | Evans et al. | |
| 5,256,133 A | 10/1993 | Spitz | |
| 5,269,783 A | 12/1993 | Sander | |
| 5,281,237 A | 1/1994 | Gimpelson | |
| 5,328,077 A | 7/1994 | Lou | |
| 5,337,736 A | 8/1994 | Reddy | |
| 5,362,294 A | 11/1994 | Seitzinger | |
| 5,366,459 A * | 11/1994 | Yoon | 606/151 |
| 5,368,595 A | 11/1994 | Lewis | |
| 5,370,650 A | 12/1994 | Tovey et al. | |
| 5,370,662 A | 12/1994 | Stone et al. | |
| 5,376,097 A | 12/1994 | Phillips | |
| 5,383,904 A | 1/1995 | Totakura et al. | |
| 5,386,836 A | 2/1995 | Biswas | |
| 5,403,328 A | 4/1995 | Shallman | |
| 5,413,598 A | 5/1995 | Moreland | |
| 5,439,467 A | 8/1995 | Benderev et al. | |
| 5,474,518 A | 12/1995 | Velazquez | |
| 5,474,543 A | 12/1995 | McKay | |
| 5,518,504 A | 5/1996 | Polyak | |
| 5,520,700 A | 5/1996 | Beyar et al. | |
| 5,520,703 A | 5/1996 | Essig | |
| 5,527,342 A | 6/1996 | Pietrzak et al. | |
| 5,544,664 A | 8/1996 | Benderev et al. | |
| 5,562,689 A | 10/1996 | Green et al. | |
| 5,571,139 A | 11/1996 | Jenkins, Jr. | |
| 5,582,188 A | 12/1996 | Benderev et al. | |
| 5,591,163 A | 1/1997 | Thompson | |
| 5,591,206 A | 1/1997 | Moufarrege | |
| 5,611,515 A | 3/1997 | Benderev et al. | |
| 5,628,756 A | 5/1997 | Barker, Jr. et al. | |
| 5,633,286 A | 5/1997 | Chen | |
| 5,643,320 A | 7/1997 | Lower et al. | |
| 5,669,935 A | 9/1997 | Rosenman et al. | |
| 5,683,349 A | 11/1997 | Makower et al. | |
| 5,697,931 A | 12/1997 | Thompson | |
| 5,709,708 A | 1/1998 | Thal | |
| 5,725,541 A | 3/1998 | Anspach, III et al. | |
| 5,741,282 A | 4/1998 | Anspach, III et al. | |
| 5,782,916 A | 7/1998 | Pintauro et al. | |
| 5,785,640 A | 7/1998 | Kresch et al. | |
| 5,803,902 A * | 9/1998 | Sienkiewicz | A61B 17/0218 |
| | | | 128/853 |
| 5,807,403 A | 9/1998 | Beyar et al. | |
| 5,836,314 A | 11/1998 | Benderev et al. | |
| 5,836,315 A | 11/1998 | Benderev et al. | |
| 5,840,011 A | 11/1998 | Landgrebe et al. | |
| 5,842,478 A | 12/1998 | Benderev et al. | |
| 5,860,425 A | 1/1999 | Benderev et al. | |
| 5,899,909 A | 5/1999 | Claren et al. | |
| 5,919,232 A | 7/1999 | Chaffringeon et al. | |
| 5,922,026 A | 7/1999 | Chin | |
| 5,925,047 A | 7/1999 | Errico et al. | |
| 5,934,283 A | 8/1999 | Willem et al. | |
| 5,935,122 A | 8/1999 | Fourkas et al. | |
| 5,944,732 A | 8/1999 | Raulerson et al. | |
| 5,954,057 A | 9/1999 | Li | |
| 5,972,000 A | 10/1999 | Beyar et al. | |
| 5,980,558 A | 11/1999 | Wiley | |
| 5,984,927 A | 11/1999 | Wenstrom, Jr. | |
| 5,988,171 A | 11/1999 | Sohn et al. | |
| 5,997,554 A | 12/1999 | Thompson | |
| 6,010,447 A | 1/2000 | Kardjian | |
| 6,027,523 A | 2/2000 | Schmieding | |
| 6,030,393 A | 2/2000 | Corlew | |
| 6,031,148 A | 2/2000 | Hayes et al. | |
| 6,036,701 A | 3/2000 | Rosenman | |
| 6,039,686 A | 3/2000 | Kovac | |
| 6,042,534 A | 3/2000 | Gellman et al. | |
| 6,042,536 A | 3/2000 | Tihon et al. | |
| 6,042,583 A | 3/2000 | Thompson et al. | |
| 6,048,351 A | 4/2000 | Gordon et al. | |
| 6,050,937 A | 4/2000 | Benderev | |
| 6,053,935 A | 4/2000 | Brenneman et al. | |
| 6,056,688 A | 5/2000 | Benderev et al. | |
| 6,068,591 A | 5/2000 | Bruckner et al. | |
| 6,071,290 A | 6/2000 | Compton | |
| 6,074,341 A | 6/2000 | Anderson et al. | |
| 6,077,216 A | 6/2000 | Benderev et al. | |
| 6,099,538 A | 8/2000 | Moses | |
| 6,099,551 A | 8/2000 | Gabbay | |
| 6,099,552 A | 8/2000 | Adams | |
| 6,106,545 A | 8/2000 | Egan | |
| 6,110,101 A | 8/2000 | Tihon et al. | |
| 6,117,067 A | 9/2000 | Gil-Vernet | |
| 6,127,597 A | 10/2000 | Beyar et al. | |
| 6,168,611 B1 | 1/2001 | Rizvi | |
| 6,200,330 B1 | 3/2001 | Benderev et al. | |
| 6,221,005 B1 | 4/2001 | Bruckner et al. | |
| 6,241,736 B1 | 6/2001 | Sater et al. | |
| 6,264,676 B1 | 7/2001 | Gellman et al. | |
| 6,273,852 B1 | 8/2001 | Lehe et al. | |
| 6,302,840 B1 | 10/2001 | Benderev | |
| 6,306,079 B1 | 10/2001 | Trabucco | |
| 6,322,492 B1 | 11/2001 | Kovac | |
| 6,328,686 B1 | 12/2001 | Kovac | |
| 6,328,744 B1 | 12/2001 | Harari et al. | |
| 6,334,446 B1 | 1/2002 | Beyar | |
| 6,352,553 B1 | 3/2002 | van der Burg et al. | |
| 6,382,214 B1 | 5/2002 | Raz et al. | |
| 6,387,041 B1 | 5/2002 | Harari et al. | |
| 6,406,423 B1 | 6/2002 | Scetbon | |

(56) References Cited

U.S. PATENT DOCUMENTS

| | | |
|---|---|---|
| 6,406,480 B1 | 6/2002 | Beyar et al. |
| 6,414,179 B1 | 7/2002 | Banville |
| 6,423,080 B1 | 7/2002 | Gellman et al. |
| 6,451,024 B1 | 9/2002 | Thompson et al. |
| 6,475,139 B1 | 11/2002 | Miller |
| 6,478,727 B2 | 11/2002 | Scetbon |
| 6,482,214 B1 | 11/2002 | Sidor, Jr. et al. |
| 6,491,703 B1 | 12/2002 | Ulmsten |
| 6,494,906 B1 | 12/2002 | Owens |
| 6,502,578 B2 | 1/2003 | Raz et al. |
| 6,506,190 B1 | 1/2003 | Walshe |
| 6,530,943 B1 | 3/2003 | Hoepffner et al. |
| 6,575,897 B1 | 6/2003 | Ory |
| 6,582,443 B2 | 6/2003 | Cabak et al. |
| 6,592,515 B2 | 7/2003 | Thierfelder |
| 6,592,610 B2 | 7/2003 | Beyar |
| 6,596,001 B2 | 7/2003 | Stormby et al. |
| 6,599,235 B2 | 7/2003 | Kovac |
| 6,599,323 B2 | 7/2003 | Melican et al. |
| 6,602,260 B2 | 8/2003 | Harari et al. |
| 6,612,977 B2 | 9/2003 | Staskin |
| 6,638,210 B2 | 10/2003 | Berger |
| 6,638,211 B2 | 10/2003 | Suslian et al. |
| 6,638,284 B1 | 10/2003 | Rousseau et al. |
| 6,641,524 B2 | 11/2003 | Kovac |
| 6,641,525 B2 | 11/2003 | Rocheleau |
| 6,648,921 B2 | 11/2003 | Anderson |
| 6,652,450 B2 | 11/2003 | Neisz et al. |
| 6,673,010 B2 | 1/2004 | Skiba et al. |
| 6,685,629 B2 | 2/2004 | Therin |
| 6,689,047 B2 | 2/2004 | Gellman et al. |
| 6,691,711 B2 | 2/2004 | Raz |
| 6,699,175 B2 | 3/2004 | Miller |
| 6,702,827 B1 | 3/2004 | Lund |
| 6,752,814 B2 | 6/2004 | Gellman et al. |
| 6,755,781 B2 | 6/2004 | Gellman |
| 6,802,807 B2 | 10/2004 | Anderson |
| 6,830,052 B2 | 12/2004 | Carter et al. |
| 6,881,184 B2 | 4/2005 | Zappala |
| 6,884,212 B2 | 4/2005 | Thierfelder et al. |
| 6,908,425 B2 | 6/2005 | Luscombe |
| 6,908,473 B2 | 6/2005 | Skiba et al. |
| 6,911,002 B2 | 6/2005 | Fierro |
| 6,911,003 B2 | 6/2005 | Anderson et al. |
| 6,932,759 B2 | 8/2005 | Kammerer |
| 6,936,052 B2 | 8/2005 | Gellman et al. |
| 6,953,428 B2 | 10/2005 | Gellman et al. |
| 6,960,160 B2 | 11/2005 | Browning |
| 6,971,986 B2 | 12/2005 | Staskin et al. |
| 6,974,462 B2 | 12/2005 | Sater |
| 6,981,944 B2 | 1/2006 | Jamiolkowski |
| 6,981,983 B1 | 1/2006 | Rosenblatt et al. |
| 6,991,597 B2 | 1/2006 | Gellman et al. |
| 7,014,607 B2 | 3/2006 | Gellman |
| 7,025,063 B2 | 4/2006 | Snitkin |
| 7,025,772 B2 | 4/2006 | Gellman et al. |
| 7,037,255 B2 | 5/2006 | Inman |
| 7,048,682 B2 | 5/2006 | Neisz et al. |
| 7,056,333 B2 | 6/2006 | Walshe |
| 7,070,556 B2 | 7/2006 | Anderson |
| 7,070,558 B2 | 7/2006 | Gellman et al. |
| 7,083,568 B2 | 8/2006 | Neisz et al. |
| 7,083,637 B1 | 8/2006 | Tannhauser |
| 7,087,065 B2 | 8/2006 | Ulmsten et al. |
| 7,112,210 B2 | 9/2006 | Ulmsten et al. |
| 7,121,997 B2 | 10/2006 | Kammerer et al. |
| 7,131,943 B2 | 11/2006 | Kammerer |
| 7,131,944 B2 | 11/2006 | Jaquetin |
| 7,175,591 B2 | 2/2007 | Kaladelfos |
| 7,198,597 B2 | 4/2007 | Siegel et al. |
| 7,226,407 B2 | 6/2007 | Kammerer |
| 7,226,408 B2 | 6/2007 | Harai et al. |
| 7,229,404 B2 | 6/2007 | Bouffier |
| 7,229,453 B2 | 6/2007 | Anderson |
| 7,235,043 B2 | 6/2007 | Gellman et al. |
| 7,261,723 B2 | 8/2007 | Smith et al. |
| 7,297,102 B2 | 11/2007 | Smith et al. |
| 7,299,803 B2 | 11/2007 | Kovac |
| 7,303,525 B2 | 12/2007 | Watschke et al. |
| 7,326,213 B2 | 2/2008 | Benderev et al. |
| 7,347,812 B2 | 3/2008 | Mellier |
| 7,351,197 B2 | 4/2008 | Montpetit et al. |
| 7,357,773 B2 | 4/2008 | Watschke et al. |
| 7,364,541 B2 | 4/2008 | Chu et al. |
| 7,371,245 B2 | 5/2008 | Evans et al. |
| 7,387,634 B2 | 6/2008 | Benderev |
| 7,393,320 B2 | 7/2008 | Montpetit et al. |
| 7,407,480 B2 | 8/2008 | Staskin |
| 7,410,460 B2 | 8/2008 | Benderev |
| 7,413,540 B2 | 8/2008 | Gellman et al. |
| 7,422,557 B2 | 9/2008 | Arnal |
| 7,431,690 B2 | 10/2008 | Merade et al. |
| 7,494,495 B2 | 2/2009 | Delorme et al. |
| 7,500,945 B2 | 3/2009 | Cox |
| 7,513,865 B2 | 4/2009 | Bourne et al. |
| 7,527,588 B2 | 5/2009 | Zaddem et al. |
| 7,588,598 B2 | 9/2009 | Delorme et al. |
| 7,601,118 B2 | 10/2009 | Smith et al. |
| 7,611,454 B2 | 11/2009 | De Leval |
| 7,621,864 B2 | 11/2009 | Suslian et al. |
| 7,637,860 B2 | 12/2009 | MacLean |
| 7,686,759 B2 | 3/2010 | Sater |
| 7,691,050 B2 | 4/2010 | Gellman et al. |
| 7,722,527 B2 | 5/2010 | Bouchier et al. |
| 7,722,528 B2 | 5/2010 | Arnal et al. |
| 7,740,576 B2 | 6/2010 | Hodroff |
| 7,753,839 B2 | 7/2010 | Siegel et al. |
| 7,762,942 B2 | 7/2010 | Neisz et al. |
| 7,766,926 B2 | 8/2010 | Bosely et al. |
| 7,789,821 B2 | 9/2010 | Browning |
| 7,981,024 B2 | 7/2011 | Levy |
| 8,172,745 B2 | 5/2012 | Rosenblatt |
| 2001/0049467 A1 | 12/2001 | Lehe et al. |
| 2002/0007222 A1 | 1/2002 | Desai |
| 2002/0028980 A1 | 3/2002 | Thierfelder et al. |
| 2002/0128670 A1 | 9/2002 | Ulmsten et al. |
| 2002/0147382 A1 | 10/2002 | Neisz et al. |
| 2002/0151762 A1 | 10/2002 | Rocheleau et al. |
| 2002/0151909 A1 | 10/2002 | Gellman et al. |
| 2002/0161382 A1 | 10/2002 | Neisz |
| 2003/0004581 A1 | 1/2003 | Rousseau |
| 2003/0036676 A1 | 2/2003 | Scetbon |
| 2003/0065402 A1 | 4/2003 | Anderson et al. |
| 2003/0176875 A1 | 9/2003 | Anderson |
| 2004/0015057 A1 | 1/2004 | Rocheleau et al. |
| 2004/0073235 A1 | 4/2004 | Lund |
| 2004/0225181 A1 | 11/2004 | Chu et al. |
| 2004/0267088 A1 | 12/2004 | Kammerer |
| 2005/0000523 A1 | 1/2005 | Beraud |
| 2005/0004427 A1 | 1/2005 | Cervigni |
| 2005/0004576 A1 | 1/2005 | Benderev |
| 2005/0038451 A1 | 2/2005 | Rao et al. |
| 2005/0055104 A1 | 3/2005 | Arnal et al. |
| 2005/0131391 A1 | 6/2005 | Chu et al. |
| 2005/0131393 A1 | 6/2005 | Chu et al. |
| 2005/0199249 A1 | 9/2005 | Karram |
| 2005/0245787 A1 | 11/2005 | Cox et al. |
| 2005/0256530 A1 | 11/2005 | Petros |
| 2005/0277806 A1 | 12/2005 | Cristalli |
| 2005/0278037 A1 | 12/2005 | Delorme et al. |
| 2005/0283189 A1 | 12/2005 | Rosenblatt et al. |
| 2006/0015010 A1 | 1/2006 | Jaffe et al. |
| 2006/0058578 A1 | 3/2006 | Browning |
| 2006/0069301 A1 | 3/2006 | Neisz et al. |
| 2006/0089524 A1 | 4/2006 | Chu |
| 2006/0089525 A1 | 4/2006 | Mamo et al. |
| 2006/0122457 A1 | 6/2006 | Kovac |
| 2006/0173237 A1 | 8/2006 | Jacquetin |
| 2006/0195007 A1 | 8/2006 | Anderson |
| 2006/0195011 A1 | 8/2006 | Arnal |
| 2006/0217589 A1 | 9/2006 | Wan et al. |
| 2006/0229493 A1 | 10/2006 | Weiser et al. |
| 2006/0229596 A1 | 10/2006 | Weiser et al. |
| 2006/0252980 A1 | 11/2006 | Arnal et al. |

(56) References Cited

U.S. PATENT DOCUMENTS

| | | |
|---|---|---|
| 2006/0287571 A1 | 12/2006 | Gozzi |
| 2007/0015953 A1 | 1/2007 | MacLean |
| 2007/0078295 A1 | 4/2007 | Landgrebe |
| 2007/0112361 A1* | 5/2007 | Schonholz et al. ......... 606/151 |
| 2007/0173864 A1 | 7/2007 | Chu |
| 2008/0039678 A1 | 2/2008 | Montpetit et al. |
| 2008/0140218 A1 | 6/2008 | Staskin et al. |
| 2008/0207988 A1 | 8/2008 | Hanes |
| 2009/0005634 A1 | 1/2009 | Rane |
| 2009/0012353 A1 | 1/2009 | Beyer |
| 2009/0192346 A1* | 7/2009 | Rosenblatt .................. 600/30 |
| 2009/0221868 A1 | 9/2009 | Evans |
| 2010/0022822 A1 | 1/2010 | Walshe |
| 2010/0174134 A1 | 7/2010 | Anderson et al. |
| 2010/0179575 A1 | 7/2010 | Von Pechmann et al. |
| 2010/0261950 A1 | 10/2010 | Lund |
| 2010/0280627 A1 | 11/2010 | Hanes, II |
| 2010/0286482 A1* | 11/2010 | Rosenblatt .......... A61B 5/0538 600/202 |
| 2010/0298630 A1 | 11/2010 | Wignall |
| 2010/0312051 A1* | 12/2010 | Brown ........................ 600/37 |
| 2011/0124954 A1 | 5/2011 | Ogdahl |
| 2011/0174313 A1 | 7/2011 | Von Pechmann et al. |
| 2012/0016185 A1 | 1/2012 | Sherts et al. |

FOREIGN PATENT DOCUMENTS

| | | |
|---|---|---|
| DE | 4220283 C2 | 5/1994 |
| DE | 10211360 | 9/2003 |
| DE | 20016866 | 3/2007 |
| EP | 0248544 A1 | 12/1987 |
| EP | 0470308 A1 | 2/1992 |
| EP | 0650703 A1 | 6/1994 |
| EP | 0643945 A2 | 7/1994 |
| EP | 0632999 A1 | 1/1995 |
| EP | 1093758 A1 | 4/2001 |
| EP | 1060714 A3 | 9/2002 |
| EP | 1342450 B1 | 9/2003 |
| FR | 2787990 A1 | 7/2000 |
| FR | 2852813 A1 | 1/2004 |
| GB | 2268690 A | 1/1994 |
| GB | 2353220 A | 10/2000 |
| IT | 1299162 | 4/1998 |
| WO | WO9317635 A1 | 9/1993 |
| WO | WO9319678 A2 | 10/1993 |
| WO | WO9511631 A1 | 5/1995 |
| WO | WO9525469 A1 | 9/1995 |
| WO | WO9716121 A1 | 5/1997 |
| WO | WO9730638 A1 | 5/1997 |
| WO | WO9747244 A1 | 12/1997 |
| WO | WO9819606 A1 | 5/1998 |
| WO | WO9835606 A1 | 8/1998 |
| WO | WO9835616 A1 | 8/1998 |
| WO | WO9835632 A1 | 8/1998 |
| WO | WO9842261 A1 | 10/1998 |
| WO | WO9853746 A1 | 12/1998 |
| WO | WO9916381 A1 | 4/1999 |
| WO | WO9937217 A1 | 7/1999 |
| WO | WO9952450 A1 | 10/1999 |
| WO | WO9953844 A1 | 10/1999 |
| WO | WO99/59477 | 11/1999 |
| WO | WO9959477 A1 | 11/1999 |
| WO | WO0064370 A1 | 2/2000 |
| WO | WO0013601 A1 | 3/2000 |
| WO | WO0018319 A1 | 4/2000 |
| WO | WO0027304 A1 | 5/2000 |
| WO | WO0040158 A2 | 7/2000 |
| WO | WO0057812 A1 | 10/2000 |
| WO | WO0066030 A1 | 11/2000 |
| WO | WO0074594 A1 | 12/2000 |
| WO | WO0074613 A1 | 12/2000 |
| WO | WO0074633 A2 | 12/2000 |
| WO | WO0106951 A1 | 2/2001 |
| WO | WO0126581 A1 | 4/2001 |
| WO | WO0139670 A1 | 6/2001 |
| WO | WO0145588 A1 | 6/2001 |
| WO | WO0145589 A1 | 6/2001 |
| WO | WO0156499 A1 | 8/2001 |
| WO | WO0228312 A1 | 4/2002 |
| WO | WO0228315 A2 | 4/2002 |
| WO | WO0230293 A1 | 4/2002 |
| WO | WO0232284 A2 | 4/2002 |
| WO | WO0234124 A2 | 5/2002 |
| WO | WO238079 A2 | 5/2002 |
| WO | WO0239890 A2 | 5/2002 |
| WO | WO02058563 A1 | 8/2002 |
| WO | WO02062237 A1 | 8/2002 |
| WO | WO02069781 | 9/2002 |
| WO | WO02071953 A2 | 9/2002 |
| WO | WO02078552 A1 | 10/2002 |
| WO | WO02089704 A2 | 11/2002 |
| WO | WO03017848 A1 | 3/2003 |
| WO | WO03003778 A1 | 4/2003 |
| WO | WO03028585 A2 | 4/2003 |
| WO | WO03037215 A2 | 5/2003 |
| WO | WO03041613 A1 | 5/2003 |
| WO | WO03047435 A1 | 6/2003 |
| WO | WO03068107 A1 | 8/2003 |
| WO | WO03075792 A1 | 9/2003 |
| WO | WO03092546 A2 | 11/2003 |
| WO | WO03096929 A1 | 11/2003 |
| WO | WO2004012626 A1 | 2/2004 |
| WO | WO2004016196 A2 | 2/2004 |
| WO | WO2004/017862 | 3/2004 |
| WO | WO2004017862 A2 | 3/2004 |
| WO | WO2004034912 A1 | 4/2004 |
| WO | WO2005079702 A1 | 4/2005 |
| WO | WO2005079702 A1 | 9/2005 |
| WO | WO2005122954 A1 | 12/2005 |
| WO | WO2006015031 A2 | 2/2006 |
| WO | WO2006108145 A1 | 10/2006 |
| WO | WO2007011341 A1 | 1/2007 |
| WO | WO2007014241 A1 | 2/2007 |
| WO | WO2007016083 A1 | 2/2007 |
| WO | WO2007027592 A2 | 3/2007 |
| WO | WO2007059199 A2 | 5/2007 |
| WO | WO2007081955 A1 | 7/2007 |
| WO | 2007097994 A2 | 8/2007 |
| WO | WO2007097994 | 8/2007 |
| WO | WO2007137226 A2 | 11/2007 |
| WO | 2007149348 A2 | 12/2007 |
| WO | WO2007146784 A2 | 12/2007 |
| WO | WO2007149348 A2 | 12/2007 |
| WO | WO2007149555 A2 | 12/2007 |
| WO | 2008057261 A2 | 5/2008 |
| WO | WO2008057261 A2 | 5/2008 |
| WO | WO2008124056 A1 | 10/2008 |
| WO | WO2009005714 A2 | 1/2009 |
| WO | 2009017680 A2 | 2/2009 |
| WO | WO 2009017680 A2 * | 2/2009 |
| WO | WO2009017680 A2 | 2/2009 |
| WO | 2011082350 A1 | 7/2011 |
| WO | WO2011/082350 | 7/2011 |

OTHER PUBLICATIONS

Advantage A/T™, Surgical Mesh Sling Kit, Boston Scientific, 6 pages (2002).

Albert H. Aldridge, B.S., M.D., F.A.C.S., Transplantation of Fascia for Relief of Urinary Stress Incontinence, American Journal of Obstetrics and Gynecology, V. 44, pp. 398-411, (1948).

Amundsen, Cindy L. et al., Anatomical Correction of Vaginal Vault Prolapse by Uterosacral Ligament Fixation in Women Who Also Require a Pubovaginal Sling, The Journal of Urology, vol. 169, pp. 1770-1774, (May 2003).

Araki, Tohru et al., The Loop-Loosening Procedure for Urination Difficulties After Stamey Suspension of the Vesical Neck, The Journal of Urology, vol. 144, pp. 319-323 (Aug. 1990).

Asmussen, M. et.al., Simultaneous Urethro-Cystometry With a New Technique, Scand J Urol Nephrol 10, p. 7-11 (1976).

Beck, Peter R. et al., Treatment of Urinary Stress Incontinence With Anterior Colporrhaphy, Obstetrics and Gynecology, vol. 59 (No. 3), pp. 269-274 (Mar. 1982).

(56) References Cited

OTHER PUBLICATIONS

Benderev, Theodore V., MD, A Modified Percutaneous Outpatient Bladder Neck Suspension System, Journal of Urology, vol. 152, pp. 2316-2320 (Dec. 1994).
Benderev, Theodore V., MD, Anchor Fixation and Other Modifications of Endoscopic Bladder Neck Suspension, Urology, vol. 40, No. 5, pp. 409-418 (Nov. 1992).
Bergman, Arieh et al., Three Surgical Procedures for Genuine Stress Incontinence: Five-Year Follow-Up of a Prospective Randomized Study, Am J Obstet Gynecol, vol. 173 No. 1, pp. 66-71 (Jul. 1995).
Blaivas, Jerry et al., Pubovaginal Fascial Sling for the Treatment of Complicated Stress Urinary Incontinence, The Journal of Urology, vol. 145, pp. 1214-1218 (Jun. 1991).
Blaivas, Jerry et al., Type III Stress Urinary Incontinence: Importance of Proper Diagnosis and Treatment, Surgical Forum, pp. 473-475, (1984).
Blaivas, Jerry, Commentary: Pubovaginal Sling Procedure, Experience with Pubovaginal Slings, pp. 93-101 (1990).
Boyles, Sarah Hamilton et al., Procedures for Urinary Incontinence in the United States, 1979-1997, Am J Obstet Gynecol, vol. 189, n. 1, pp. 70-75 (Jul. 2003).
Bryans, Fred E., Marlex Gauze Hammock Sling Operation With Cooper's Ligament Attachment in the Management of Recurrent Urinary Stress Incontinence, American Journal of Obstetrics and Gynecology, vol. 133, pp. 292-294 (Feb. 1979).
Burch, John C., Urethrovaginal Fixation to Cooper's Ligament for Correction of Stress Incontinence, Cystocele, and Prolapse, Am. J. Obst. & Gyn, vol. 31, pp. 281-290 (1961).
Capio™ CL—Transvaginal Suture Capturing Device—Transvaginal Suture Fixation to Cooper's Ligament for Sling Procedures, Boston Scientific, Microvasive®, 8 pages, (2002).
Cervigni, Mauro et al., The Use of Synthetics in the Treatment of Pelvic Organ Prolapse, Voiding Dysfunction and Female Urology, vol. 11, pp. 429-435 (2001).
Choe, Jong M. et al., Gore-Tex Patch Sling: 7 Years Later, Urology, vol. 54, pp. 641-646 (1999).
Cook/Ob Gyn®, Urogynecology, Copyright Cook Urological Inc., pp. 1-36 (1996).
Dargent, D. et al., Insertion of a Suburethral Sling Through the Obturator Membrane in the Treatment of Female Urinary Incontinence, Gynecol Obstet Fertil, vol. 30, pp. 576-582 (2002).
Das, Sakti et al., Laparoscopic Colpo-Suspension, The Journal of Urology, vol. 154, pp. 1119-1121 (Sep. 1995).
Debodinance, Philipp et al., "Tolerance of Synthetic Tissues in Touch With Vaginal Scars: Review to the Point of 287 Cases", European Journal of Obstetrics & Gynecology and Reproductive Biology 87 (1999) pp. 23-30.
Decter, Ross M., Use of the Fascial Sling for Neurogenic Incontinence: Lessons Learned, The Journal of Urology, vol. 150, pp. 683-686 (Aug. 1993).
Delancey, John, MD, Structural Support of the Urethra As It Relates to Stress Urinary Incontinence: The Hammock Hypothesis, Am J Obstet Gynecol, vol. 170 No. 6, pp. 1713-1723 (Jun. 1994).
Delorme, Emmanuel, Trans-Obturator Sling: A Minimal Invasive Procedure to Treat Female Stress Urinary Incontinence, Progres en Urologie, vol. 11, pp. 1306-1313 (2001) English Abstract attached.
Diana, et al., Treatment of Vaginal Vault Prolapse With Abdominal Sacral Colpopexy Using Prolene Mesh, American Journal of Surgery, vol. 179, pp. 126-128, (Feb. 2000).
Eglin et al., Transobturator Subvesical Mesh. Tolerance and short-term results of a 103 case continuous series, Gynecologie Obstetrique & Fertilite, vol. 31, Issue 1, pp. 14-19 (Jan. 2003).
Enzelsberger, H. et al., Urodynamic and Radiologic Parameters Before and After Loop Surgery for Recurrent Urinary Stress Incontinence, Acta Obstet Gynecol Scand, 69, pp. 51-54 (1990).
Eriksen, Bjarne C. et al., Long-Term Effectiveness of the Burch Colposuspension in Female Urinary Stress Incontinence, Acta Obstet Gynecol Scand, 69, pp. 45-50 (1990).

Falconer, C. et al., Clinical Outcome and Changes in Connective Tissue Metabolism After Intravaginal Slingplasty in Stress Incontinence Women, International Urogynecology Journal, pp. 133-137 (1966).
Falconer, C. et al., Influence of Different Sling Materials of Connective Tissue Metabolism in Stress Urinary Incontinent Women, International Urogynecology Journal, Supp. 2, pp. S19-S23 (2001).
Farnsworth, B.N., Posterior Intravaginal Slingplasty (Infracoccygeal Sacropexy) for Sever Posthysterectomy Vaginal Vault Prolapse—A Preliminary Report on Efficacy and Safety, Int Urogynecology J, vol. 13, pp. 4-8 (2002).
Farquhar, Cynthia M. et al., Hysterectomy Rates in the United States 1990-1997, Obstetrics & Gynecology, vol. 99, n. 2, pp. 229-234 (Feb. 2002).
Fidela, Marie R. et al., Pelvic Support Defects and Visceral and Sexual Function in Women Treated With Sacrospinous Ligament Suspension and Pelvic Reconstruction, Am J Obstet Gynecol, vol. 175, n. 6 (Dec. 1996).
Flood, C.G. et al., Anterior Colporrhaphy Reinforce With Marlex Mesh for the Treatment of Cystoceles, International Urogynecology Journal, vol. 9, pp. 200-204 (1998).
Gilja, Ivan et al., A Modified Raz Bladder Neck Suspension Operation (Transvaginal Burch), The Journal of Urology, vol. 153, pp. 1455-1457 (May 1995).
Gittes, Ruben F. et al., No-Incision Pubovaginal Suspension for Stress Incontinence, The Journal of Urology, vol. 138 (Sep. 1987).
Guner, et al., Transvaginal Sacrospinous Colpopexy for Marked Uterovaginal and Vault Prolapse, Inter J of Gynec & Obstetrics, vol. 74, pp. 165-170 (2001).
Gynecare TVT Tension-Free Support for Incontinence, The tension-free solution to female Incontinence, Gynecare Worldwide, 6 pages, (2002).
Handa, Victoria L. et al, Banked Human Fascia Lata for the Suburethral Sling Procedure: A Preliminary Report, Obstetrics & Gynecology, vol. 88 No. 6, 5 pages (Dec. 1996).
Heit, Michael et al., Predicting Treatment Choice for Patients With Pelvic Organ Prolapse, Obstetrics & Gynecology, vol. 101, n. 6, pp. 1279-1284 (Jun. 2003).
Henriksson, L. et al., A Urodynamic Evaluation of the Effects of Abdominal Urethrocystopexy and Vaginal Sling Urethroplasty in Women With Stress Incontinence, Am. J. Obstet. Gynecol. vol. 131, No. 1, pp. 77-82 (Mar. 1, 1978).
Hodgkinson, C. Paul et.al., Urinary Stress Incontinence in the Female, Department of Gynecology and Obstetrics, Henry Ford Hospital, vol. 10, No. 5, p. 493-499, (Nov. 1957).
Holschneider, C. H., et al., The Modified Pereyra Procedure in Recurrent Stress Urinary Incontinence: A 15-year Review, Obstetrics & Gynecology, vol. 83, No. 4, pp. 573-578 (Apr. 1994).
Horbach, Nicollette S., et al., Instruments and Methods, A Suburethral Sling Procedure with Polytetrafluoroethylene for the Treatment of Genuine Stress Incontinence in Patients with Low Urethral Closure Pressure, Obstetrics & Gynecology, vol. 71, No. 4, pp. 648-652 (Apr. 1998).
Ingelman-Sunberg, A. et al., Surgical Treatment of Female Urinary Stress Incontinence, Contr. Gynec. Obstet., vol. 10, pp. 51-69 (1983).
IVS Tunneller—A Universal instrument for anterior and posterior intra-vaginal tape placement, Tyco Healthcare, 4 pages (Aug. 2002).
IVS Tunneller—ein universelles Instrument fur die Intra Vaginal Schlingenplastik, Tyco Healthcare, 4 pages (2001).
Jeffcoate, T.N.A. et al., The Results of the Aldridge Sling Operation for Stress Incontinence, Journal of Obstetrics and Gynaecology, pp. 36-39 (1956).
Jones, N.H.J. Reay et al., Pelvic Connective Tissue Resilience Decreases With Vaginal Delivery, Menopause and Uterine Prolapse, Br J Surg, vol. 90, n. 4, pp. 466-472 (Apr. 2003).
Julian, Thomas, The Efficacy of Marlex Mesh in the Repair of Sever, Recurrent Vaginal Prolapse of the Anterior Midvaginal Wall, Am J Obstet Gynecol, vol. 175, n. 6, pp. 1472-1475 (Dec. 1996).
Karram, Mickey et al., Patch Procedure: Modified Transvaginal Fascia Lata Sling for Recurrent for Severe Stress Urinary Incontinence, vol. 75, pp. 461-463 (Mar. 1990).

(56) References Cited

OTHER PUBLICATIONS

Karram, Mickey M. et al., Chapter 19 Surgical Treatment of Vaginal Vault Prolapse, Urogynecology and Reconstructive Pelvic Surgery, (Walters & Karram eds.) pp. 235-256 (Mosby 1999).

Kersey, J., The Gauze Hammock Sling Operation in the Treatment of Stress Incontintence, British Journal of Obstetrics and Gynaecology, vol. 90, pp. 945-949 (Oct. 1983).

Klutke, Carl et al., The Anatomy of Stress Incontinence: Magentic Resonance Imaging of the Female Bladder Neck and Urethra, The Journal of Urology, vol. 143, pp. 563-566 (Mar. 1990).

Klutke, John James et al., Transvaginal Bladder Neck Suspension to Cooper's Ligament: A Modified Pereyra Procedure, Obstetrics & Gynecology, vol. 88, No. 2, pp. 294-296 (Aug. 1996).

Klutke, John M.D. et al, The promise of tension-free vaginal tape for female SUI, Contemporary Urology, 7 pages (Oct. 2000).

Korda, A. et al., Experience With Silastic Slings for Female Urinary Incontience, Aust NZ J. Obstet Gynaecol, vol. 29, pp. 150-154 (May 1989).

Kovac, S. Robert, et al, Pubic Bone Suburethral Stabilization Sling for Recurrent Urinary Incontinence, Obstetrics & Gynecology, vol. 89, No. 4, pp. 624-627 (Apr. 1997).

Kovac, S. Robert, et al, Pubic Bone Suburethral Stabilization Sling: A Long Term Cure for SUI?, Contemporary OB/GYN, 10 pages (Feb. 1998).

Kovac, S. Robert, Follow-up of the Pubic Bone Suburethral Stabilization Sling Operation for Recurrent Urinary Incontinence (Kovac Procedure), Journal of Pelvic Surgery, pp. 156-160 (May 1999).

Kovac, Stephen Robert, M.D., Cirriculum Vitae, pp. 1-33 (Jun. 18, 1999).

Leach, Gary E., et al., Female Stress Urinary Incontinence Clinical Guidelines Panel Report on Surgical Management of Female Stress Urinary Incontinence, American Urological Association, vol. 158, pp. 875-880 (Sep. 1997).

Leach, Gary E., MD, Bone Fixation Technique for Transvaginal Needle Suspension, Urology vol. XXXI, No. 5, pp. 388-390 (May 1988).

Lichtenstein, Irving L. et al, The Tension Free Hernioplasty, The American Journal of Surgery, vol. 157 pp. 188-193 (Feb. 1989).

Loughlin, Kevin R. et al., Review of an 8-Year Experience With Modifications of Endoscopic Suspension of the Bladder Neck for Female Stress Incontinence, The Journal of Uroloyg, vol. 143, pp. 44-45 (1990).

Luber, Karl M. et al., The Demographics of Pelvic Floor Disorders; Current Observations and Future Projections, Am J Obstet Gynecol, vol. 184, n. 7, pp. 1496-1503 (Jun. 2001).

Mage, Technique Chirurgicale, L'Interpostion D'Un Treillis Synthetique Dans La Cure Par Vote Vaginale Des Prolapsus Genitaux, J Gynecol Obstet Biol Reprod, vol. 28, pp. 825-829 (1999).

Marchionni, Mauro et al., True Incidence of Vaginal Vault Prolapse—Thirteen Years of Experience, Journal of Reproductive Medicine, vol. 44, n. 8, pp. 679-684 (Aug. 199).

Marinkovic, Serge Peter et al., Triple Compartment Prolapse: Sacrocolpopexy With Anterior and Posterior Mesh Extensions, Br J Obstet Gynaecol, vol. 110, pp. 323-326 (Mar. 2003).

Marshall, Victor Fray et al. The Correction of Stress Incontinence by Simple Vesicourethral Suspension, Surgery, Gynecology and Obstetrics, vol. 88, pp. 509-518 (1949).

McGuire, Edward J. et al., Pubovaginal Sling Procedure for Stress Incontinence, The Journal of Urology, vol. 119, pp. 82-84 (Jan. 1978).

McGuire, Edward J. et al., Abdominal Procedures for Stress Incontinence, Urologic Clinics of North America, pp. 285-290, vol. 12, No. 2 (May 1985).

McGuire, Edward J. et al., Experience With Pubovaginal Slings for Urinary Incontinence At the University of Michigan, Journal of Urology, vol. 138, pp. 90-93(1987).

McGuire, Edwared J. et al., Abdominal Fascial Slings, Slings, Raz Female Urology, p. 369-375 (1996).

McGuire™ Suture Buide, The McGuire™ Suture Guide, a single use instrument designed for the placement of a suburethral sling, Bard, 2 pages (2001).

McIndoe, G. A. et al., The Aldridge Sling Procedure in the Treatment of Urinary Stress Incontinence, Aust. N Z Journal of Obstet Gynecology, pp. 238-239 (Aug. 1987).

McKiel, Charles F. Jr., et al, Marshall-Marchetti Procedure Modification, vol. 96, pp. 737-739 (Nov. 1966).

Migliari, Roberto et al., Tension-Free Vaginal Mesh Repair for Anterior Vaginal Wall Prolapse, Eur Urol, vol. 38, pp. 151-155 (Oct. 1999).

Migliari, Roberto et al., Treatment Results Using a Mixed Fiber Mesh in Patients With Grade IV Cystocele, Journal of Urology, vol. 161, pp. 1255-1258 (Apr. 1999).

Moir, J. Chassar et.al., The Gauze-Hammock Operation, The Journal of Obstetrics and Gynaecology of British Commonwealth, vol. 75 No. 1, pp. 1-9 (Jan. 1968).

Morgan, J. E., A Sling Operation, Using Marlex Polypropylene Mesh, for the Treatment of Recurrent Stress Incontinence, Am. J. Obst. & Gynecol, pp. 369-377 (Feb. 1970).

Morgan, J. E. et al., The Marlex Sling Operation for the Treatment of Recurrent Stress Urinary Incontinence: A 16-Year Review, American Obstetrics Gynecology, vol. 151, No. 2, pp. 224-226 (Jan. 1998).

Morley, George W. et al., Sacrospinous Ligament Fixations for Eversion of the Vagina, Am J Obstet Gyn, vol. 158, n. 4, pp. 872-881 (Apr. 1988).

Narik, G. et.al., A Simplified Sling Operation Suitable for Routine Use, Gynecological and Obstetrical Clinic, University of Vienna, vol. 84, No. 3, p. 400-405, (Aug. 1, 1962).

Natale, F. et al., Tension Free Cystocele Repair (TCR): Long-Term Follow-Up, International Urogynecology Journal, vol. 11, supp. 1, p. S51 (Oct. 2000).

Nichols, David H., The Mersilene Mesh Gauze-Hammock for Severe Urinary Stress Incontinence, Obstetrics and Gynecology, vol. 41, pp. 88-93 (Jan. 1973).

Nicita, Giulio, A New Operation for Genitourinary Prolapse, Journal of Urology, vol. 160, pp. 741-745 (Sep. 1998).

Niknejad, Kathleen et al., Autologous and Synthetic Urethral Slings for Female Incontinence, Urol Clin N Am, vol. 29, pp. 597-611 (2002).

Norris, Jeffrey P. et al., Use of Synthetic Material in Sling Surgery: A Minimally Invasive Approach, Journal of Endourology, vol. 10, pp. 227-230 (Jun. 1996).

O'Donnell, Pat, Combined Raz Urethral Suspension and McGuire Pubovaginal Sling for Treatment of Complicated Stress Urinary Incontinence, Journal Arkansas Medical Society, vol. 88, pp. 389-392 (Jan. 1992).

Ostergard, Donald R. et al., Urogynecology and Urodynamics Theory and Practice, pp. 569-579 (1996).

Paraiso et al., Laparoscopic Surgery for Enterocele, Vaginal Apex Prolapse and Rectocele, Int. Urogynecol J, vol. 10, pp. 223-229 (1999).

Parra, R. O., et al, Experience With a Simplified Technique for the Treatment of Female Stress Urinary Incontinence, British Journal of Urology, pp. 615-617 (1990).

Pelosi, Marco Antonio III et al., Pubic Bone Suburethral Stabilization Sling: Laparoscopic Assessment of a Transvaginal Operation for the Treatment of Stress Urinary Incontinence, Journal of Laparoendoscopic & Advaned Surgical Techniques, vol. 9, No. 1 pp. 45-50 (1999).

Pereyra, Armand J. et al, Pubourethral Supports in Perspective: Modified Pereyra Procedure for Urinary Incontinence, Obstetrics and Gynecology, vol. 59, No. 5, pp. 643-648 (May 1982).

Pereyra, Armand J., M.D., F.A.C.S., A Simplified Surgical Procedure for Correction of Stress Incontinence in Women, West.J.Surg., Obst. & Gynec, p. 223-226, (Jul.-Aug. 1959).

Peter E. Papa Petros et al., Cure of Stress Incontinence by Repair of External Anal Sphincter, Acta Obstet Gynecol Scand, vol. 69, Sup 153, p. 75 (1990).

Peter Petros et al., Anchoring the Midurethra Restores Bladder-Neck Anatomy and Continence, The Lancet, vol. 354, pp. 997-998 (Sep. 18, 1999).

(56) References Cited

OTHER PUBLICATIONS

Petros, Peter E. Papa et al., An Anatomical Basis for Success and Failure of Female Incontinence Surgery, Scandinavian Journal of Neurourology and Urodynamics, Sup 153, pp. 55-60 (1993).
Petros, Peter E. Papa et al., An Analysis of Rapid Pad Testing and the History for the Diagnosis of Stress Incontinence, Acta Obstet Gynecol Scand, vol. 71, pp. 529-536 (1992).
Petros, Peter E. Papa et al., An Integral Theory of Female Urinary Incontinence, Acta Obstetricia et Gynecologica Scandinavica, vol. 69 Sup. 153, pp. 7-31 (1990).
Petros, Peter E. Papa et al., Bladder Instability in Women: A Premature Activation of the Micturition Reflex, Scandinavian Journal of Neurourology and Urodynamics, Sup 153, pp. 235-239 (1993).
Petros, Peter E. Papa et al., Cough Transmission Ratio: An Indicator of Suburethral Vaginal Wall Tension Rather Than Urethral Closure, Acta Obstet Gynecol Scand, vol. 69, Sup 153, pp. 37-39 (1990).
Petros, Peter E. Papa et al., Cure of Urge Incontinence by the Combined Intravaginal Sling and Tuck Operation, Acta Obstet Gynecol Scand, vol. 69, Sup 153, pp. 61-62 (1990).
Petros, Peter E. Papa et al., Further Development of the Intravaginal Slingplasty Procedure—IVS III—(With Midline "Tuck"), Scandinavian Journal of Neurourology and Urodynamics, Sup 153, p. 69-71 (1993).
Petros, Peter E. Papa et al., Medium-Term Follow-Up of the Intravaginal Slingplasty Operation Indicates Minimal Deterioration of Urinary Continence With Time, (3 pages) (1999).
Petros, Peter E. Papa et al., Non Stress Non Urge Female Urinary Incontinence—Diagnosis and Cure: A Preliminary Report, Acta Obstet Gynecol Scand, vol. 69, Sup 153, pp. 69-70 (1990).
Petros, Peter E. Papa et al., Part I: Theoretical, Morphological, Radiographical Correlations and Clinical Perspective, Scandinavian Journal of Neurourology and Urodynamics, Sup 153, pp. 5-28 (1993).
Petros, Peter E. Papa et al., Part II: The Biomechanics of Vaginal Tissue and Supporting Ligaments With Special Relevance to the Pathogenesis of Female Urinary Incontinence, Scandinavian Journal of Neurourology and Urodynamics, Sup 153, pp. 29-40 plus cover sheet (1993).
Petros, Peter E. Papa et al., Part III: Surgical Principles Deriving From the Theory, Scandinavian Journal of Neurourology and Urodynamics, Sup 153, pp. 41-52 (1993).
Petros, Peter E. Papa et al., Part IV: Surgical Appliations of the Theory—Development of the Intravaginal Sling Pklasty (IVS) Procedure, Scandinavian Journal of Neurourology and Urodynamics, Sup 153, pp. 53-54 (1993).
Petros, Peter E. Papa et al., Pelvic Floor Rehabilitation According to the Integrated Theory of Female Urinary Incontinence, Chapter 7, pp. 249-258 (book chapter).
Petros, Peter E. Papa et al., Pinch Test for Diagnosis of Stress Urinary Incontinence, Acta Obstet Gynecol Scand, vol. 69, Sup 153, pp. 33-35 (1990).
Petros, Peter E. Papa et al., Pregnancy Effects on the Intravaginal Sling Operation, Acta Obstet Gynecol Scand, vol. 69, Sup 153, pp. 77-79 (1990).
Petros, Peter E. Papa et al., The Autogenic Ligament Procedure: A Technique for Planned Formation of an Artificial Neo-Ligament, Acta Obstet Gynecol Scand, vol. 69, Sup 153, pp. 43-51 (1990).
Petros, Peter E. Papa et al., The Combined Intravaginal Sling and Tuck Operation an Ambulatory Procedure for Cure of Stress and Urge Incontinence, Acta Obstet Gynecol Scand, vol. 69, Sup 153, pp. 53-59 (1990).
Petros, Peter E. Papa et al., The Development of the Intravaginal Slingplasty Procedure: IVS II—(With Bilateral "Tucks"), Scandinavian Journal of Neurourology and Urodynamics, Sup 153, pp. 61-67 (1993).
Petros, Peter E. Papa et al., The Free Graft Procedure for Cure of the Tethered Vagina Syndrome, Scandinavian Journal of Neurourology and Urodynamics, Sup 153, pp. 85-87(1993).
Petros, Peter E. Papa et al., The Further Development of the Intravaginal Slingplasty Procedure—IVS IV—(With "Double Breasted" Unattached Vaginal Flap Repair and "Free" Vaginal Tapes), Scandinavian Journal of Neurourology and Urodynamics, Sup 153, p. 73-75 (1993).
Petros, Peter E. Papa et al., The Further Development of the Intravaginal Slingplasty Procedure—IVS V—(With "Double Breasted" Unattached Vaginal Flap Repair and Permanent Sling)., Scandinavian Journal of Neurourology and Urodynamics, Sup 153, pp. 77-79 (1993).
Petros, Peter E. Papa et al., The Intravaginal Slingplasty Operation, A Minimally Invasive Technique for Cure of Urinary Incontinence in the Female, Aust. NZ J Obstet Gynaecol, vol. 36, n. 4, pp. 453-461 (1996).
Petros, Peter E. Papa et al., The Intravaginal Slingplasty Procedure: IVS VI—Further Development of the "Double Breasted" Vaginal Flap Repair—Attached Flap, Scandinavian Journal of Neurourology and Urodynamics, Sup 153, pp. 81-84 (1993).
Petros, Peter E. Papa et al., The Posterior Fornix Syndrome: A Multiple Symptom Complex of Pelvic Pain and Abnormal Urinary Symptoms Deriving From Laxity in the Posterior Fornix of Vagina, Scandinavian Journal of Neurourology and Urodynamics, Sup 153, pp. 89-93 (1993).
Petros, Peter E. Papa et al., The Role of a Lax Posterior Vaginal Fornix in the Causation of Stress and Urgency Symptoms: A Preliminary Report, Acta Obstet Gynecol Scand, vol. 69, Sup 153, pp. 71-73 (1990).
Petros, Peter E. Papa et al., The Tethered Vagina Syndrome, Post Surgical Incontinence and I-Plasty Operation for Cure, Acta Obstet Gynecol Scand, vol. 69, Sup 153, pp. 63-67 (1990).
Petros, Peter E. Papa et al., The Tuck Procedure: A Simplified Vaginal Repair for Treatment of Female Urinary Incontinence, Acta Obstet Gynecol Scand, vol. 69, Sup 153, pp. 41-42 (1990).
Petros, Peter E. Papa et al., Urethral Pressure Increase on Effort Originates From Within the Urethra, and Continence From Musculovaginal Closure, Scandinavian Journal of Neurourology and Urodynamics, pp. 337-350 (1995).
Petros, Peter E. Papa, Development of Generic Models for Ambulatory Vaginal Surgery—Preliminary Report,International Urogynecology Journal, pp. 20-27 (1998).
Petros, Peter E. Papa, New Ambulatory Surgical Methods Using an Anatomical Classification of Urinary Dysfunction Improve Stress, Urge and Abnormal Emptying, Int. Urogynecology Journal Pelvic Floor Dystfunction, vol. 8 (5), pp. 270-278, (1997).
Petros, Peter E. Papa, Vault Prolapse II; Restoration of Dynamic Vaginal Supports by Infracoccygeal Sacropexy, an Axial Day-Case Vaginal Procedure, Int Urogynecol J, vol. 12, pp. 296-303 (2001).
Rackley, Raymond R. et al., Tension-Free Vaginal Tape and Percutaneous Vaginal Tape Sling Procedures, Techniques in Urology, vol. 7, No. 2, pp. 90-100 (2001).
Rackley, Raymond R. M.D., Synthetic Slings: Five Steps for Successful Placement, Urology Times, p. 46,48,49 (Jun. 2000).
Raz, Shlomo, et al., The Raz Bladder Neck Suspension Results in 206 Patients, The Journal of Urology, pp. 845-846 (1992).
Raz, Shlomo, Female Urology, pp. 80-86, 369-398, 435-442 (1996).
Raz, Shlomo, MD, Modified Bladder Neck Suspension for Female Stress Incontinence, Urology, vol. XVII, No. 1, pp. 82-85 (Jan. 1981).
Richardson, David A. et al., Delayed Reaction to the Dacron Buttress Used in Urethropexy, The Journal of Reproductive Medicine, pp. 689-692, vol. 29, No. 9 (Sep. 1984).
Richter, K., Massive Eversion of the Vagina: Pathogenesis, Diagnosis and Therapy of the "True" Prolapse of the Vaginal Stump, Clin obstet gynecol, vol. 25, pp. 897-912 (1982).
Ridley, John H., Appraisal of the Goebell-Frangenheim-Stoeckel Sling Procedure, American Journal Obst & Gynec., vol. 95, No. 5, pp. 741-721 (Jul. 1, 1986).
Roberts, Henry, M.D., Cystourethrography in Women, Deptment of Obstetrics and Gynaecology, University of Liverpool, May 1952, vol. XXXV, No. 293, pp. 253-259.
Sabre™ Bioabsorbable Sling, Generation Now, Mentor, 4 pages (May 2002).
Sabre™ Surgical Procedure, Mentor, 6 pages (Aug. 2002).

(56) References Cited

OTHER PUBLICATIONS

Sanz, Luis E. et al., Modification of Abdominal Sacrocolpopexy Using a Suture Anchor System, The Journal of Reproductive Medicine, vol. 48, n. 7, pp. 496-500 (Jul. 2003).
Seim, Arnfinn et al., A Study of Female Urinary Incontinence in General Practice—Demography, Medical History, and Clinical Findings, Scand J Urol Nephrol, vol. 30, pp. 465-472 (1996).
Sergent, F. et al., Prosthetic Restoration of the Pelvic Diaphragm in Genital Urinary Prolapse Surgery: Transobturator and Infacoccygeal Hammock Technique, J Gynecol Obstet Biol Reprod, vol. 32, pp. 120-126 (Apr. 2003).
Sloan W. R. et al., Stress Incontinence of Urine: A Retrospective Study of the Complications and Late Results of Simple Suprapubic Suburethral Fascial Slings, The Journal of Urology, vol. 110, pp. 533-536 (Nov. 1973).
Spencer, Julia R. et al., A Comparison of Endoscopic Suspension of the Vesical Neck With Suprapubic Vesicourethropexy for Treatment of Stress Urinary Incontinence, The Journal of Urology, vol. 137, pp. 411-415 (Mar. 1987).
Stamey, Thomas A., M.D., Endoscopic Suspension of the Vesical Neck for Urinary Incontinence in Females, Ann. Surgery, vol. 192 No. 4, pp. 465-471 (Oct. 1980).
Stanton, Stuart L., Suprapubic Approaches for Stress Incontinence in Women, Journal of American Geriatrics Society, vol. 38, No. 3, pp. 348-351 (Mar. 1990).
Stanton, Stuart, Springer-Veglag, Surgery of Female Incontinence, pp. 105-113 (1986).
Staskin, David R. et al., The Gore-Tex Sling Procedure for Female Sphincteric Incontinence: Indications, Technique, and Results, World Journal of Urology, vol. 15, pp. 295-299 (1997).
Studdiford, William E., Transplantation of Abdominal Fascia for the Relief of Urinary Stress Incontinence, American Journal of Obstetrics and Gynecology, pp. 764-775 (1944).
Subak, Leslee L. et al., Cost of Pelvic Organ Prolapse Surgery in the United States, Obstetrics & Gynecology, vol. 98, n. 4, pp. 646-651 (Oct. 2001).
Sullivan, Eugene S. et al., Total Pelvic Mesh Repair a Ten-Year Experience, Dis. Colon Rectum, vol. 44, No. 6, pp. 857-863 (Jun. 2001).
Swift, S.E., et al., Case-Control Study of Etiologic Factors in the Development of Sever Pelvic Organ Prolapse, Int Urogynecol J, vol. 12, pp. 187-192 (2001).
TVT Tension-free Vaginal Tape, Gynecare, Ethicon, Inc., 23 pages (1999).
Ulmsten, U. et al., A Multicenter Study of Tension-Free Vaginal Tape (TVT) for Surgical Treatment of Stress Urinary Incontinence, International Urogynecology Journal, vol. 9, pp. 210-213 (1998).
Ulmsten, U. et al., An Ambulatory Surgical Procedure Under Local Anesthesia for Treatment of Female Urinary Incontinence, International Urogynecology Journal, vol. 7, pp. 81-86 (May 1996).
Ulmsten, U., Female Urinary Incontinence—A Symptom, Not a Urodynamic Disease. Some Theoretical and Practical Aspects on the Diagnosis a Treatment of Female Urinary Incontinence, International Urogynecology Journal, vol. 6, pp. 2-3 (1995).
Ulmsten, Ulf et al., A Three Year Follow Up of Tension Free Vaginal Tape for Surgical Treatment of Female Stress Urinary Incontinence, British Journal of Obstetrics and Gynaecology, vol. 106, pp. 345-350 (1999).
Ulmsten, Ulf et al., Different Biochemical Composition of Connective Tissue in Continent, Acta Obstet Gynecol Scand, pp. 455-457 (1987).
Ulmsten, Ulf et al., Intravaginal Slingplasty (IVS): An Ambulatory Surgical Procedure for Treatment of Female Urinary Incontinence, Scand J Urol Nephrol, vol. 29, pp. 75-82 (1995).
Ulmsten, Ulf et al., The Unstable Female Urethra, Am. J. Obstet. Gynecol., vol. 144 No. 1, pp. 93-97 (Sep. 1, 1982).
Vesica® Percutaneous Bladder Neck Stabilization Kit, A New Approach to Bladder Neck Suspenison, Microvasive® Boston Scientific Corporation, 4 pages (1995).
Vesica® Sling Kits, Simplifying Sling Procedures, Microvasive® Boston Scientific Corporation, 4 pages (1998).
Villet, R., Réponse De R. Villet À L'Article De D. Dargent et al., Gynécolgie Obstétrique & Fertilité, vol. 31, p. 96 (2003).
Visco, Anthony G. et al., Vaginal Mesh Erosion After Abdominal Sacral Colpopexy, Am J Obstet Gynecol, vol. 184, n. 3, pp. 297-302 (297-302).
Walters, Mark D., Percutaneous Suburethral Slings: State of the Art, Presented at the conference of the American Urogynecologic Society, Chicago, 29 pages (Oct. 2001).
Waxman, Steve et al., Advanced Urologic Surgery for Urinary Incontinence, The Female Patient, pp. 93-100, vol. 21 (Mar. 1996).
Weber, Anne M. et al., Anterior Vaginal Prolapse: Review of Anatomy and Techniques of Surgical Repair, Obstetrics and Gynecology, vol. 89, n. 2, pp. 311-318 (Feb. 1997).
Webster, George et al., Voiding Dysfunction Following Cystourethropexy: ITS Evaluation and Management, The Journal of Urology, vol. 144, pp. 670-673 (Sep. 1990).
Winter, Chester C., Peripubic Urethropexy for Urinary Stress Incontinence in Women, Urology, vol. XX, No. 4, pp. 408-411 (Oct. 1982).
Winters et al., Abdominal Sacral Colpopexy and Abdominal Enterocele Repair in the Management of Vaginal Vault Prolapse, Urology, vol. 56, supp. 6A, pp. 55-63 (2000).
Woodside, Jeffrey R. et al., Suprapubic Endoscopic Vesical Neck Suspension for the Management of Urinary Incontinence in Myelodysplastic Girls, The Journal of Urology, vol. 135, pp. 97-99 (Jan. 1986).
Zacharin, Robert et al., Pulsion Enterocele: Long-Term Results of an Abdominoperineal Technique, Obstetrics & Gynecology, vol. 55 No. 2, pp. 141-148 (Feb. 1980).
Zacharin, Robert, The Suspensory Mechanism of the Female Urethra, Journal of Anatomy, Vol, 97, Part 3, pp. 423-427 (1963).
Zimmern, Phillippe E. et al., Four-Corner Bladder Neck Suspension, Vaginal Surgery for the Urologist, vol. 2, No. 1, pp. 29-36 (Apr. 1994).
Le point sur l'incontinence urinaire, Expertise et Practiques en Urologie, No. 3. Dr. Sophie Conquy [Hospital Cochin, Paris]. pp. 17-19.
Mouly, Patrick et al., Vaginal Reconstruction of a Complete Vaginal Prolapse: The Trans Obturator Repair, Journal of Urology, vol. 169, p. 183 (Apr. 2003).
Pourdeyhimi, B, Porosity of Surgical Mesh Fabrics: New Technology, J. Biomed. Mater. Res.: Applied Biomaterials, vol. 23, No. A1, pp. 145-152 (1989).
Drutz, H.P. et al., Clinical and Urodynamic Re-Evaluation of Combined Abdominovaginal Marlex Sling Operations for Recurrent Stress Urinary Incontinence, International Urogynecology Journal, vol. 1, pp. 70-73 (1990).
Petros, Papa PE et al., An Integral Theory and Its Method for the Diagnosis and Management of Female Urinary Incontinence, Scandinavian Journal of Urology and Nephrology, Supplement 153: p. 1 (1993).
Horbach, Nicollette, Suburethral Sling Procedures, Genuine Stress Incontinence, Chapter 42, pp. 569-579.
Mentor Porges, Uratape, ICS/IUGA Symp, Jul. 2002.

\* cited by examiner

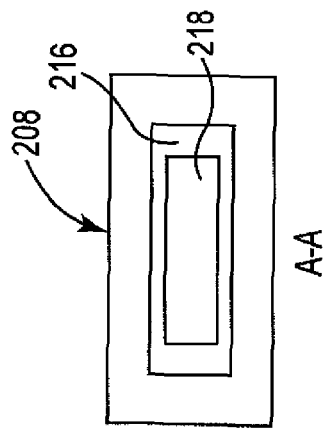
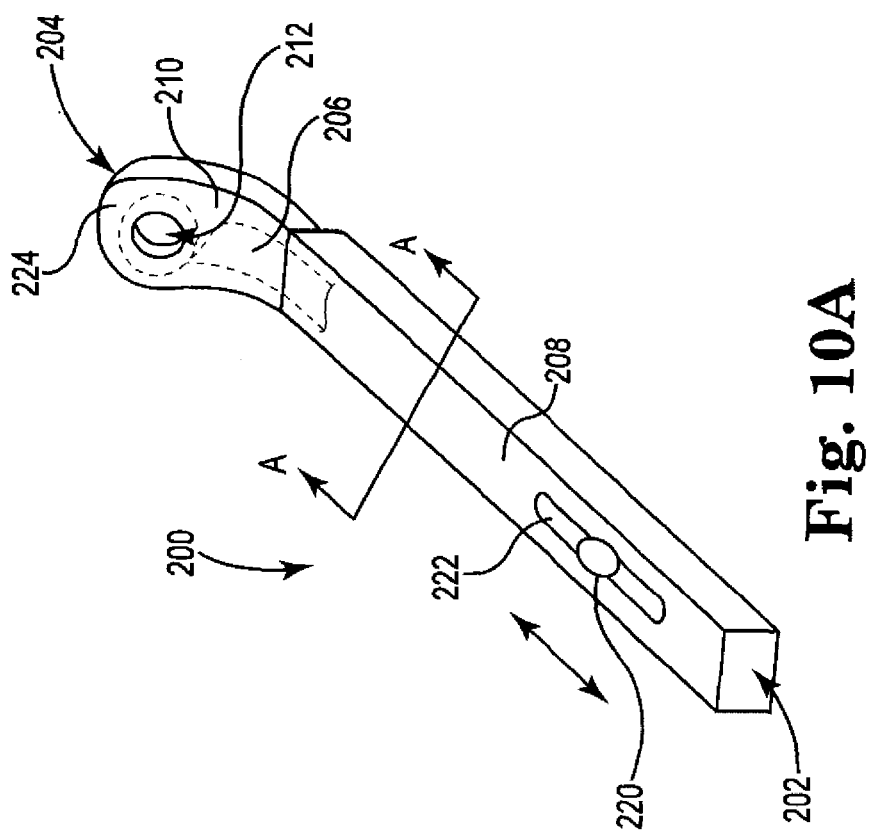
Fig. 10B
Fig. 10A

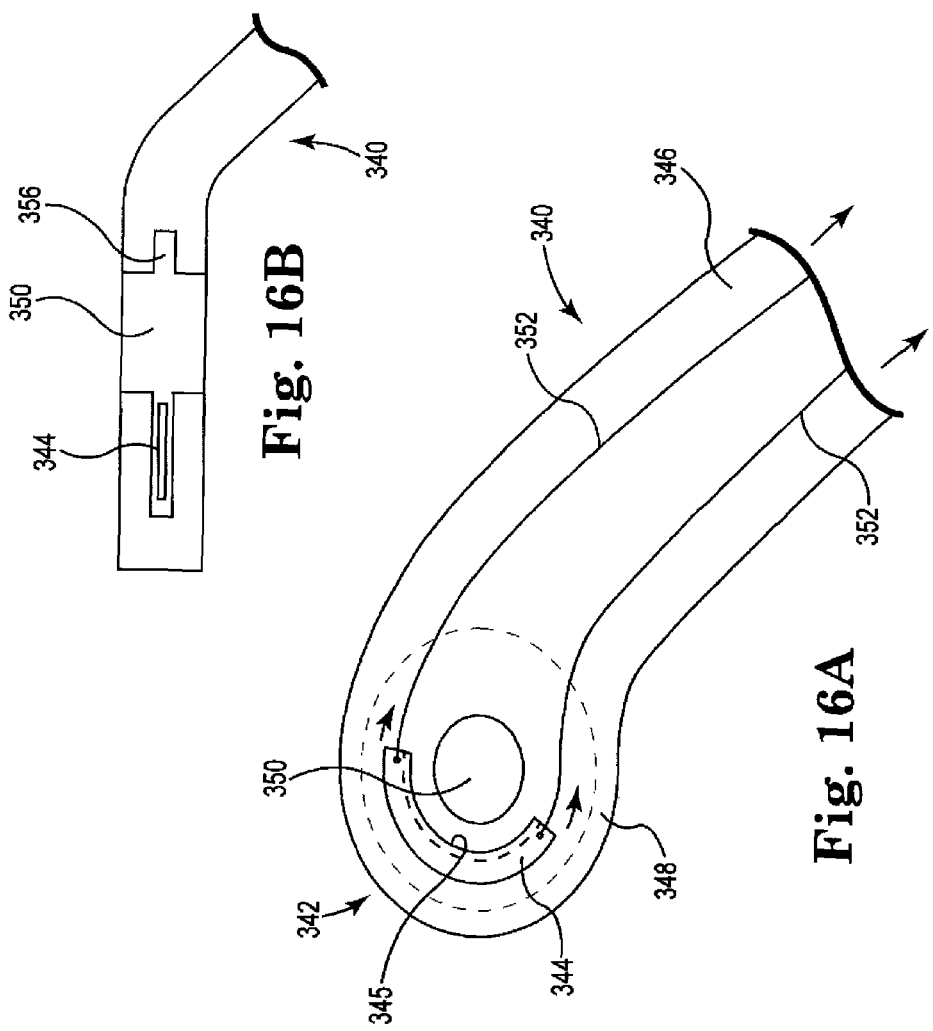

TOOLS AND METHODS FOR TREATMENT OF PELVIC CONDITIONS

CROSS-REFERENCE TO RELATED APPLICATIONS

This application claims the benefit under 35 U.S.C. §119 (e) of U.S. Provisional Patent Application No. 61/515,160, filed Aug. 4, 2011, titled "Tools and Methods for Treatment of Pelvic Conditions", and U.S. Provisional Patent Application No. 61/515,698, filed Aug. 5, 2011, titled "Tools and Methods for Treatment of Pelvic Conditions," both of which are incorporated herein by reference in their entireties.

FIELD OF THE INVENTION

The present invention relates to tools and related methods for treating pelvic conditions by use of a pelvic implant to support pelvic tissue. The pelvic treatments include, for example, treatment of vaginal prolapse by laparoscopic, abdominal, and transvaginal procedures, and treatment of urethral incontinence (e.g., stress urinary incontinence) by a single incision retropubic procedure.

BACKGROUND

Pelvic health for men and women is a medical area of increasing importance, at least in part due to an aging population. Examples of common pelvic ailments include incontinence (e.g., fecal and urinary incontinence), pelvic tissue prolapse (e.g., female vaginal prolapse), and other conditions that affect the pelvic floor. Pelvic disorders such as these can be caused by weakness or damage to normal pelvic support systems. Common etiologies include childbearing, removal of the uterus, connective tissue defects, prolonged heavy physical labor, and postmenopausal atrophy.

Urinary incontinence can further be classified as including different types, such as stress urinary incontinence (SUI), urge urinary incontinence, mixed urinary incontinence, among others. Urinary incontinence can be characterized by the loss or diminution in the ability to maintain the urethral sphincter closed as the bladder fills with urine. Male or female stress urinary incontinence (SUI) generally occurs when the patient is physically stressed.

Pelvic floor disorders include cystocele, rectocele, and prolapse such as anal, uterine, and vaginal vault prolapse. Vaginal vault prolapse is a condition that occurs when the upper portion of the vagina loses its normal shape and moves downwardly into the vaginal canal. In its severest forms, vaginal vault prolapse can result in the distension of the vaginal apex outside of the vagina. Vaginal vault prolapse may occur alone, such as can be caused by weakness of the pelvic and vaginal tissues and muscles, or can be associated with a rectocele, cystocele and/or enterocele. A rectocele is caused by a weakening or stretching of tissues and muscles that hold the rectum in place, which can result in the rectum moving from its usual location to a position where it presses against the back wall of the vagina. A cystocele is a hernia of the bladder, usually into the vagina and introitus. An enterocele is a vaginal hernia in which the peritoneal sac containing a portion of the small bowel extends into the rectovaginal space. All of these conditions can represent challenging forms of pelvic disorders for surgeons to treat. Some of these treatments include, for example, abdominal sacralcolpopexy (SCP), which may be performed laparoscopically, and transvaginal sacralcolpopexy (TSCP), wherein these procedures are performed using a variety of different instruments, implants, and surgical methods. It is known to repair vaginal vault prolapse by suturing the vaginal vault (e.g., by stitches) to the supraspinous ligament or by attaching the vaginal vault through mesh or fascia to the sacrum.

There is ongoing need to provide physicians with improved methods and associated instruments for treating pelvic conditions including incontinence, vaginal prolapse (e.g., vaginal vault prolapse), and other pelvic organ prolapse conditions, wherein such methods can include those that are minimally invasive, safe, and highly effective.

SUMMARY

Tools, systems, and methods as described herein can be used to treat pelvic conditions such as incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), and other conditions caused by muscle and ligament weakness, hysterectomies, and the like. In accordance with the invention, sacral colpopexy procedures can be performed through an abdominal opening, laparoscopically, or transvaginally, which procedures will require different approaches, each of which can use certain embodiments of devices and/or methods of the invention.

In a sacral colpopexy procedure it is desirable to simplify the process of attaching an implant within a patient using implantation devices or tools having various features. Recently, multi-piece implants have been developed for supporting pelvic tissue (e.g., vaginal tissue, urethral tissue, etc.). These multi-piece implants can include at least two pieces (e.g., an extension portion piece and support portion piece) engaged with each other at an adjustment area or feature. Other implants can include those that are Y-shaped, which include a base member and two support members extending from the base member, wherein the attachment of portions of the Y-shaped implant can be adjustable relative to their respective attachment points within a patient (e.g., the sacrum). Devices or tools of the invention described herein can be referred to as adjusting and/or cutting tools, which provide methods for adjusting this engagement between two pieces of an adjustable implant or between an implant and an anchor or attachment point, and/or then cutting a portion of the implant with the same tool. Useful features of these adjusting and cutting tools can include a shaft that extends between a proximal end and a distal end, where the proximal end can be manipulated outside of the patient and the distal end includes an adjusting feature that can contact two pieces of the implant to allow adjustment between the two pieces. The distal end of the tool can also include a cutting mechanism to allow the distal end to be used to cut a component of the implant without having to utilize a separate tool.

Devices described herein can be referred to as adjustment tools, which provide methods for adjusting lengths of extension portions of an implant. Such adjustment tools can include features for engagement with self-fixating eyelets in which the eyelet/mesh interface is completely contained within the lumen of a cylinder at the end of the adjustment tool during tensioning. The adjustment tools may also simplify adjustment that can be inhibited when eyelets cannot be "backed out" of the mesh to reduce tension, such as if over-tensioning of the implant has occurred during the implantation procedure. The adjustment tool may further include a flexible rubber gasket placed in the lumen of the end cylinder that covers prong features on the locking eyelet. In this way, the positioning of the mesh can be better controlled (i.e., prevented from becoming entangled) during tensioning. With the use of such an instrument, a surgeon can find the appropriate tension for the implant prior to securing the self-fixating eyelet to the mesh.

Various surgical tools, implants, and procedural improvements are also disclosed herein that involve separate tensioning to the anterior and posterior compartments in a sacral colpopexy procedure, and may additionally involve single arm tensioning to prevent or minimize twisting. Certain embodiments of methods and implants described herein involve the use of a Y-shaped mesh component that is designed to fixate to the sacral promontory, and may additionally include two apical mesh pieces that are sutured to the anterior and posterior vaginal walls. Embodiments of implants and methods can involve placement of an implant to support pelvic tissue, by way of an incision of minimum size.

Certain embodiments relate generally to fixation of attachment devices or anchors and related methods for placing a pelvic mesh implant, and methods for treating pelvic conditions such as incontinence, vaginal prolapse, and other conditions caused by muscle and ligament weakness. Embodiments of the implants can include a tissue support portion and one or more anchors, arms and the like. In addition, disclosed are combination devices (implants, tools, and anchors, etc.) and related methods useful for anterior or posterior prolapse repair with other treatments for pelvic floor disorders such as urinary incontinence, pelvic floor decent (levator avulsion), and/or sacral fixation. Exemplary levator and support devices can be introduced through a vaginal incision to tie in with conventional transvaginal mesh repairs and other applications, for example, or can be introduced abdominally (e.g., laparoscopically). After implantation, an adjusting or cutting tool can be used to optimize the length and/or positioning of components relative to each other and then the components can be cut, if desired.

Additional embodiments of the invention include an adjusting and cutting tool for use in a method for placing an adjustable implant to support tissue (e.g., vaginal tissue). Such a tool may be able to place a distal end that includes both a cutting structure and an adjusting structure at a location near a target tissue, such as tissue of a vaginal vault. An adjusting and cutting tools of the invention can be an elongate tool that includes a distal end that engages an elongate portion of an implant (e.g., an elongate mesh or rod portion of an extension portion piece of an adjustable multi-piece implant) to allow manipulation of the elongate portion, for adjustment and cutting of the elongate portion after adjustment. Advantages of such an adjusting and cutting tool can include safe and controlled cutting action of a portion of an implant, preventing tissue damage and trauma; and a controlled cut that can ensure a desired length of implant remaining at the adjusting engagement.

BRIEF DESCRIPTION OF THE DRAWINGS

The present invention will be further explained with reference to the appended Figures, wherein like structure is referred to by like numerals throughout the several views, and wherein:

FIGS. 10A and 10B are perspective and sectional views of an exemplary embodiment of an adjusting and cutting tool of the invention;

FIGS. 16A and 16B are perspective and side cross-sectional views, respectively, of an exemplary embodiment of an adjusting and cutting tool of the invention;

DETAILED DESCRIPTION

Figure 1:
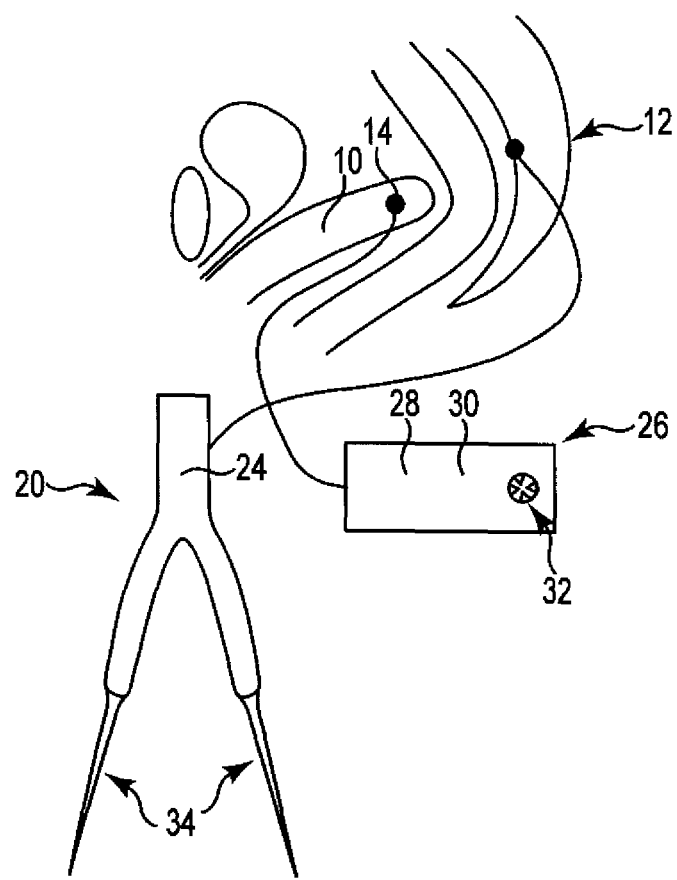
FIG. 1 is a schematic view of a Y-shaped implant as it can be positioned relative to a patient's anatomy, and that can be used in accordance with tools of the invention.

The methods and tools as described can be useful in procedures for supporting vaginal tissue, including but not limited to sacral colpopexy procedures (e.g., transvaginal and abdominal), along with procedures for treating vaginal vault prolapse caused by rectocele, cystocele, enterocele, and other causes. A sacral colpopexy is a procedure for providing vaginal vault suspension, which can be accomplished with the use of an implant such as a strip of mesh or other material of posterior vaginal tissue (e.g., a vaginal cuff) to a region or component of sacral anatomy such as the sacrum (bone itself), a nearby sacrospinous ligament, uterosacral ligament, or anterior longitudinal ligament at the sacral promontory, such as may be accomplished using bone screws that are implanted into the sacrum. Sacral colpopexy may be performed through an abdominal incision, a vaginal incision, or laparoscopically. An implant, such as a synthetic mesh, can be carefully customized or assembled into a special shape by the surgeon. In some sacral colpopexy procedures that also involve a hysterectomy, an implant can alternatively be attached to posterior vaginal tissue that remains after removal of the uterus and cervix, and also to anatomy to support the vaginal tissue at or around the sacrum, such as to uterosacral ligaments or to the sacrum itself (i.e., to a component of the sacral anatomy).

As used herein, the term "anchor" refers non-specifically to any structure that can connect an implant to tissue of a pelvic region. The tissue may be bone or a soft tissue such as a muscle, fascia, ligament, tendon, or the like. Certain methods, implants, and anchors of the present description can incorporate a helical anchor such as a screw or coil that can be inserted (e.g., driven) into tissue, preferably soft tissue such as an anterior longitudinal ligament, by rotating about a longitudinal axis upon which the helical anchor advances into the tissue in a longitudinal direction. Other methods may include an anchor in the form of a "self-fixating tip," which can be inserted by pushing the anchor into an engagement site using a straight or curved needle.

Embodiments of the invention are directed generally to surgical instruments, assemblies, and implantable articles for treating pelvic floor disorders such as various forms of prolapse. According to embodiments described herein, a surgical implant can be used to treat a pelvic condition, including the specific examples of surgically placing a surgical implant to treat a pelvic condition such as vaginal vault prolapse. Described herein are various features of surgical implants, surgical tools, surgical systems, surgical kits, and surgical methods useful for installing implants.

As described at Applicant's copending patent application U.S. Ser. No. 12/308,436, filed Oct. 29, 2010, now U.S. Pat. No. 8,834,350; U.S. Ser. No. 12/669,099, filed May 13, 2010, now U.S. Pat. No. 8,597,173; and International Application No. PCT/US2010/062577, filed Dec. 30, 2010, the entire disclosures of which are incorporated herein by reference, implants useful for vaginal tissue repair (e.g., vaginal prolapse), such as by sacral colpopexy procedures, may include multiple pieces and may be adjustable. Exemplary implants may include multiple pieces with adjustable engagements for supporting vaginal vault tissue by connecting the tissue (through the implant) to a component of sacral anatomy, such as an extension portion piece and a support portion piece. An extension portion piece can be connected at one end by an anchor (e.g., a self-fixating tip or a helical anchor) to tissue of a pelvic region, such as at a component of sacral anatomy. A second end of the extension portion piece can be connected, by way of an adjusting engagement, to the support portion piece. The adjusting engagement may include a frictional engagement element such as a grommet, a one-way or a two-way frictional adjusting element, or the like. The support portion piece, in turn, can contact and support tissue, such as vaginal tissue, in treating vaginal prolapse.

The methods and tools as described can be useful in procedures for surgical placement of a pelvic implant, including but not limited to sacral colpopexy procedures, to support tissue or a urethra, or to support other tissue of a pelvic region by transvaginal placement of the implant. Exemplary procedures include transvaginal sacral colpopexy procedures and single incision retropubic procedures for treating urinary incontinence. A single incision retropubic sling procedure is a procedure for implanting a urethral sling below a urethra, with supportive ends connecting tissue in a retropubic region. The procedure uses a single incision in vaginal tissue to access the retropubic region, and the implant can include a multi-piece adjustable implant that includes two ends, each including a soft tissue anchor. The soft tissue anchors at each end can be placed in soft tissue in the retropubic space, and the sling can be placed below a urethra and adjusted.

Referring now to the Figures, where like structure may be described with like reference numbers and/or terms, and initially to FIG. 1, an embodiment is illustrated of an exemplary implant, tool, and method related to providing support for an apex of a vagina 10 by fixation and support from a component of sacral anatomy, using an adjustable implant. This embodiment comprises a Y-shaped implant 20 having a posterior portion 24 for attaching to a sacrum (i.e., a component of sacral anatomy such as an anterior longitudinal ligament) that is generally designated by reference numeral 12, and two mesh or polymeric rod arms 34 that can be routed through an aperture (e.g., a locking eyelet 32) on each of two anterior or support portions 26, which are attachable to vaginal wall tissue to support a vaginal apex. An exemplary attachment area to the vagina 10 is indicated by point 14. Anterior or support portions 26 include an anterior area 28 for attachment to a vaginal wall and a posterior area 30 that includes an eyelet 32 for adjustably engaging one each of the two arms 34. With implant 20 secured to a component of sacral anatomy, and each of anterior support portions 26 attached to vaginal wall tissue, each arm 34 can be led through one of eyelets 32. A tool, such as an adjusting and cutting tool of the invention, can then be used to push the eyelet 32 up the arm 34 and attached mesh, until a specific tension has been reached. Such a tool can then cut off any undesired, excess length of arm 34 or attached mesh material.

An adjustment tool for use in a method as described, such as for suitable placement of an adjustable implant to support vaginal tissue (e.g., for a sacral colpopexy that is performed surgically, laparoscopically, or transvaginally), can be a tool that is able to place a distal end of an implant at a useful location (e.g., transvaginally, near vaginal tissue such as tissue of a vaginal vault). Such an adjustment tool can be an elongate tool that includes a distal end that engages an elongate portion of an implant (e.g., an elongate mesh or rod portion of an extension portion piece of an adjustable multi-piece implant) to allow manipulation of the elongate portion, for adjustment thereof.

Figure 2:
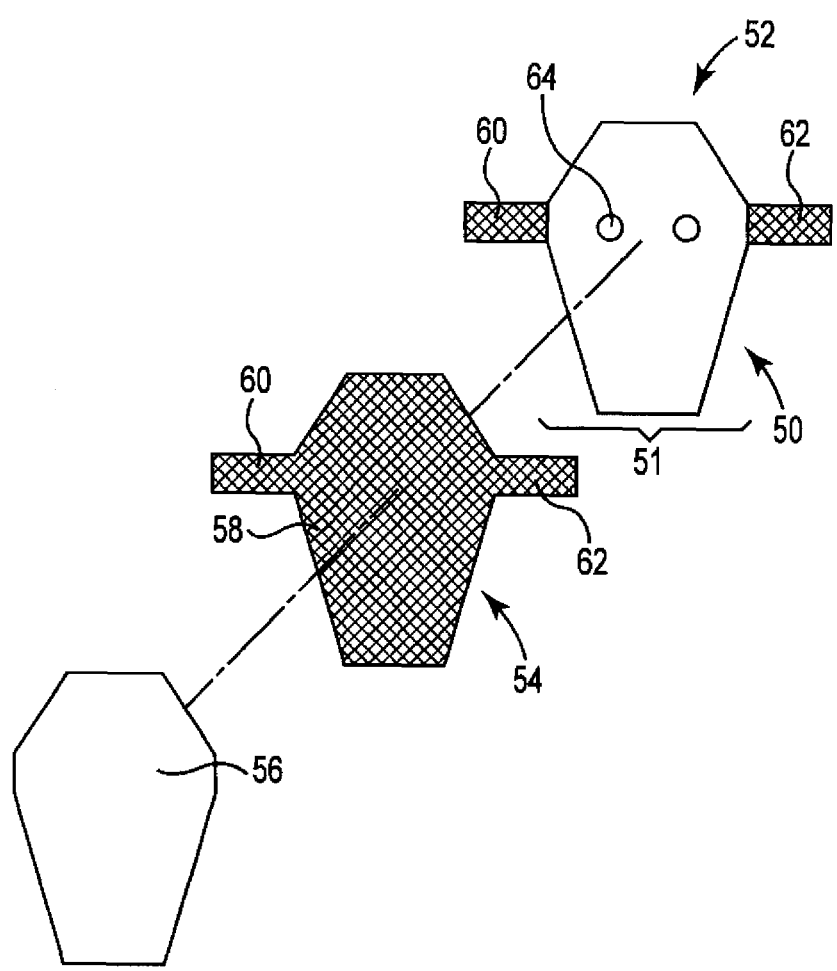
FIG. 2 is an exploded front view of an exemplary implant that can be used in accordance with tools of the invention.
Figure 3:
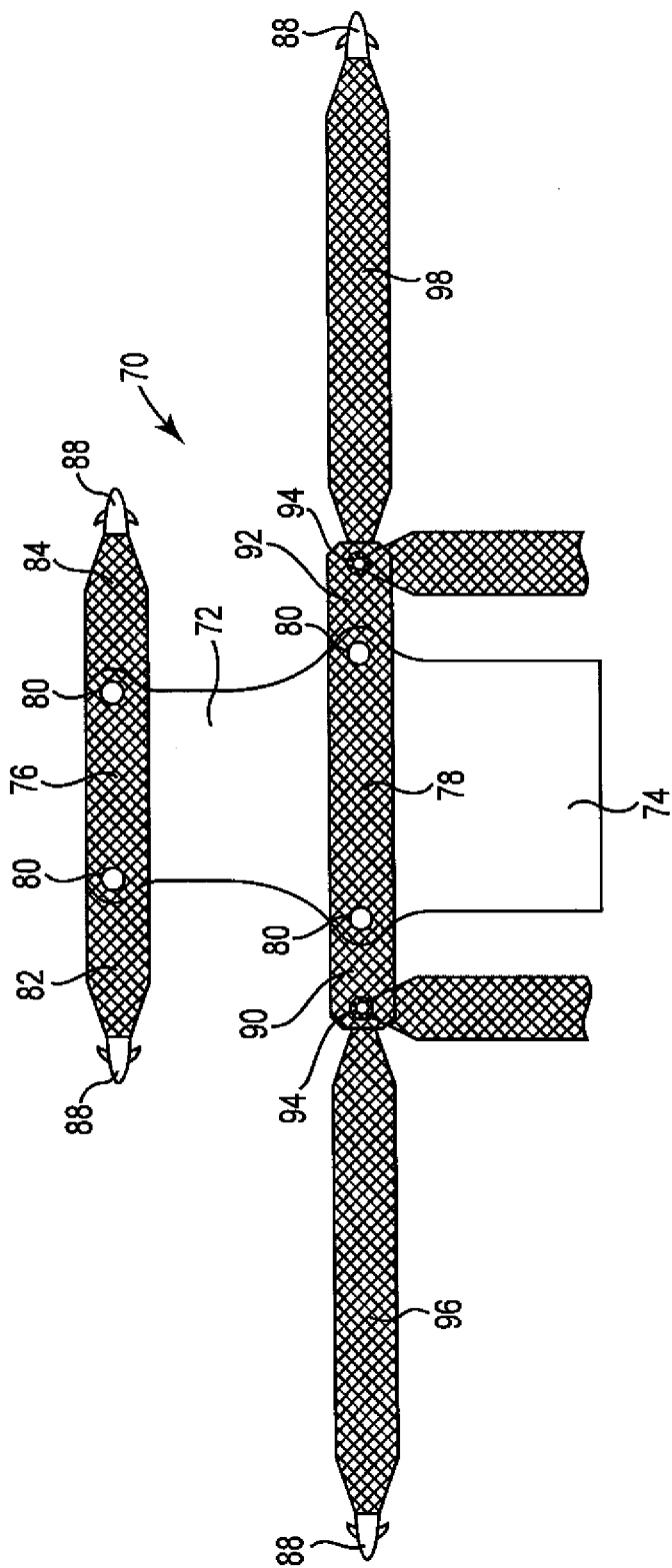
FIG. 3 is a front view of an exemplary implant that can be used in accordance with tools of the invention.
Figure 4:
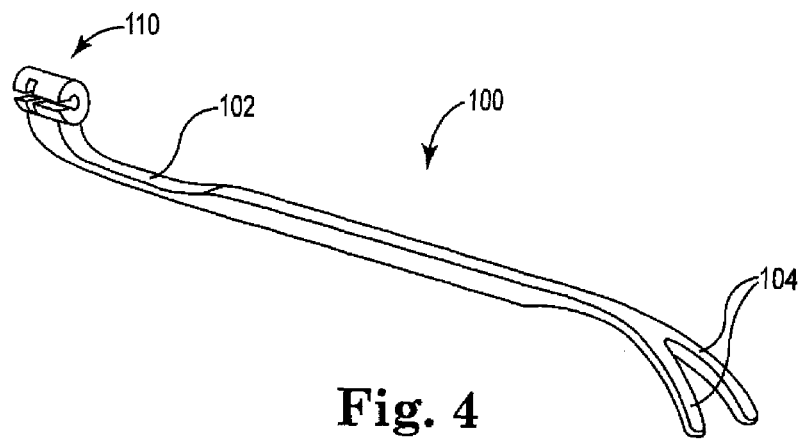
FIG. 4 is a perspective view of an exemplary adjusting and cutting tool of the invention.
Figures 5, 6:
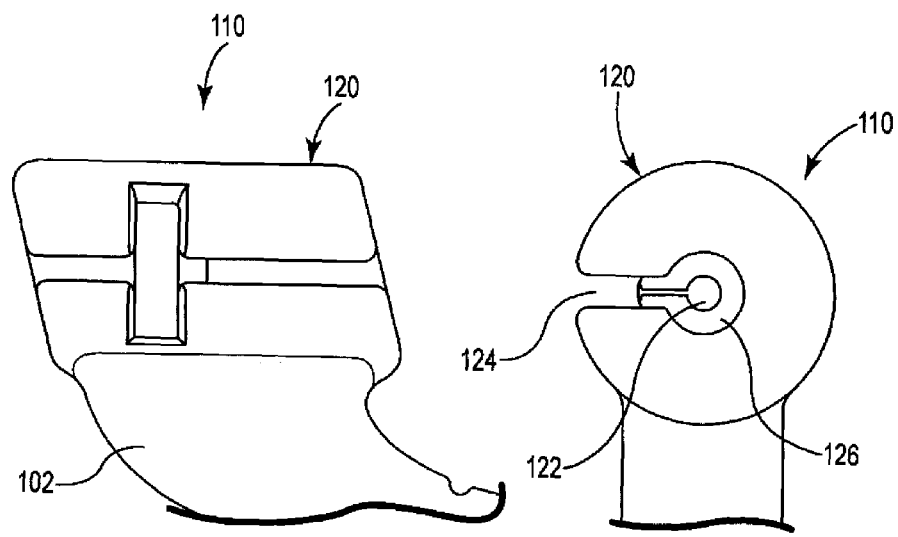
FIG. 5 is an enlarged front view of a distal end of the tool illustrated in FIG. 4.
FIG. 6 is an end view of the distal end of the tool illustrated in FIG. 5.

Additional embodiments of exemplary pelvic implants that can be implanted and/or adjusted with the assistance of adjustment tools of the invention are illustrated in FIGS. 2 and 3. These figures show pelvic implants that include a multi-layer or hybrid tissue support portion (or support portion piece) made of two layers. One of the layers can be a synthetic layer and a second of the layers can be a biologic layer, for example, which are described and illustrated in Applicant's co-pending U.S. patent application Ser. No. 12/308,436, the entire contents of which is incorporated herein by reference. Optionally, the hybrid tissue support portion may be incorporated into any implant, such as into a support portion section of a multi-piece implant that also includes extension portions and a frictional adjusting element as described. Such pelvic implants can also be adjustable using an adjustment tool of the invention.

In more particularity, FIG. 2 illustrates a portion of an exemplary pelvic implant 50 as an exploded view. Implant 50 includes support portion piece 52 that includes tissue support portion 51 and support portion piece arms 60 and 62. Tissue support portion 51 includes a layer 54 that can be made of a synthetic material such as mesh, and a layer 56 that can be made of a biologic material such as porcine, cadaveric, etc. Layer 54 includes first and second support portion piece arms 60 and 62 extending from a tissue support portion 58. Support portion piece arms 60, 62 can be connected (e.g., adjustably) to extension portion pieces (not shown) to form the implant 50. As illustrated, layer 56 generally has the same size and shape as the tissue support portion 58 of layer 54. Layer 56 can be attached to layer 54 by any useful fastener, such as polymeric rivets 64 in one or more locations, or alternately by using sutures, staples, heat bonding, adhesive, etc. When used in a patient, layer 56 can be positioned to contact sensitive tissue, such as vaginal tissue.

FIG. 3 illustrates another exemplary hybrid or multi-layer implant 70 that can be implanted and/or adjusted with the assistance of tools of the invention. Implant 70 may be useful for treating anterior vaginal prolapse such as cystocele, optionally in combination with symptoms of urinary incontinence, for example. Implant 70 includes a support portion piece 72 that includes a tissue support portion 74, which may be made of biologic material or mesh, along with first and second bands 76 and 78 (e.g., mesh bands) that can be attached to support portion piece 72 with rivets 80 or other fasteners. Superior or "anterior" mesh band 76, as attached to support portion piece 72, provides first and second non-adjustable superior mesh extension portions 82 and 84, each, as illustrated, having a tissue fastener (e.g., self-fixating tip) 88 at a distal end thereof. Superior extension portions 82 and 84 may be designed to support the anterior portion of implant 70, which can support one or more of vaginal tissue, the bladder neck, or urethra, to treat vaginal prolapse and optionally to relieve symptoms of incontinence. Each tissue fastener 88 can be implanted at tissue of the obturator foramen, for example. Alternately, superior extension portions 82 and 84 can be longer and may reach to a retropubic space, an abdominal incision, the pubic bone, or through an obturator foramen and to an external incision at the inner thigh. Superior extension portions 82 and 84 are shown to be of a fixed length, but could alternately be adjustable as described herein.

The second mesh band 78, which is shown as being attached to the support portion piece 72, provides first and second support portion piece arms 90 and 92, each having a frictional adjusting element 94 secured to a distal end. First and second inferior extension portion pieces 96 and 98, having tissue fasteners (e.g., self-fixating tips) 88 at distal ends thereof, are adjustably connected to frictional adjusting element 94, as illustrated.

With the above-described implants, along with other implants used for treatment of pelvic conditions, an insertion tool can be used to install the implant. Various types of insertion tools are known, and these types of tools and modifications thereof can be used according to this description to install an implant. Examples of useful tools include those types of tool that generally include a thin elongate shaft (e.g., needle) that attaches to a handle; a handle attached to one end (a proximal end) of the shaft; and an optional distal end (or "end tip") of the shaft adapted to engage an end of an extension portion, e.g., a self-fixating tip. The needle can facilitate placement of the distal end of the extension portion at a desired anatomical location, that may be internal or through a tissue path to an external incision.

Exemplary insertion tools for treatment of incontinence and vaginal prolapse are described, e.g., in U.S. Ser. No. 10/834,943, now U.S. Pat. No. 7,500,945; U.S. Ser. No. 10/306,179, now U.S. Pat. No. 7,070,556; U.S. Ser. No. 11/347,553, now U.S. Pat. No. 7,422,557; U.S. Ser. No. 11/398,368, now U.S. Pat. No. 7,740,576; U.S. Ser. No. 10/840,646, now U.S. Pat. No. 7,351,197; PCT application number 2006/028828; and PCT application number 2006/0260618; each of which is incorporated herein by reference. Tools described in these documents are designed for placement of an implant in a pelvic region for the treatment of prolapse, male or female incontinence, etc. The tools may be curved in two or three dimensions, and may include, for example, a helical portion in three dimensions for placing an extension portion of an implant through a tissue path that passes from a region of the urethra, through an obturator foramen, to an external incision in the groin or inner thigh area. Other described insertion tools include a two-dimensional elongate needle that allows a user to place an extension portion of an implant through an external incision in the perirectal or coccyx region of the lower back and buttock area.

Exemplary insertion tools can be similar to or can include features of tools described in the above-referenced documents. For use according to certain methods described herein, those insertion tools may be modified, such as to allow the insertion tool to be used to place a self-fixating tip at tissue within the pelvic region through a tissue path that does not extend to an external incision. The insertion tool can be designed, shaped, and sized, to include an elongate shaft that may be straight or that may be curved in two or three dimensions, that can be inserted through a vaginal incision (for female anatomy) or through a perineal incision (for male anatomy), and extend from that incision to or through pelvic tissue for placement of a distal end of an extension portion.

In accordance with embodiments of the invention, an implant can be secured at a desired location in a patient, and then adjusted with the assistance of an adjustment tool that helps to move one or more portions of the implant relative to each other. Such an exemplary adjustment tool generally includes an end cylinder that can receive an extension portion of an implant. In use, such as when a self-fixating tip is anchored in tissue, the adjustment tool can be slid along an extension portion piece until the distal end of tool contacts an adjusting element. Further movement of adjustment tool can then adjust the distance between the self-fixating tip and a support portion piece to reduce the length of the extension portion of implant.

FIGS. 4-7 illustrate an exemplary embodiment of an adjustment tool 100, which can be used for adjusting lengths of extension portions of an implant. Tool 100 includes an elongated body 102 having two prongs 104 at its proximal end and a cylinder 120 at its distal end 110. Cylinder 120 includes a central opening 122 extending through its length, in which a gasket 126 (e.g., a rubber gasket) is positioned. Cylinder 120 further includes an open-ended slot or gap 124 that extends from the central opening 122 to the outer surface of the cylinder 120. The slot or gap 124 can be slid over an extension portion of an implant (e.g., a mesh support portion piece arm) and used to adjust the length of the extension portion (e.g., a distance between a tissue fastener and a tissue support portion of a support portion piece). The inner surface of central opening 122 can engage with a surface of a frictional adjusting element to provide adjustment of a length of the extension portion. The slot or gap 124 allows the extension portion to be fed into the central opening 122 at any desired location along a length of the extension portion, and then that extension portion can be moved proximally or distally to adjust the location of the elongate portion or piece relative to another piece of the adjustable implant (e.g., a support portion piece).

Figure 7:
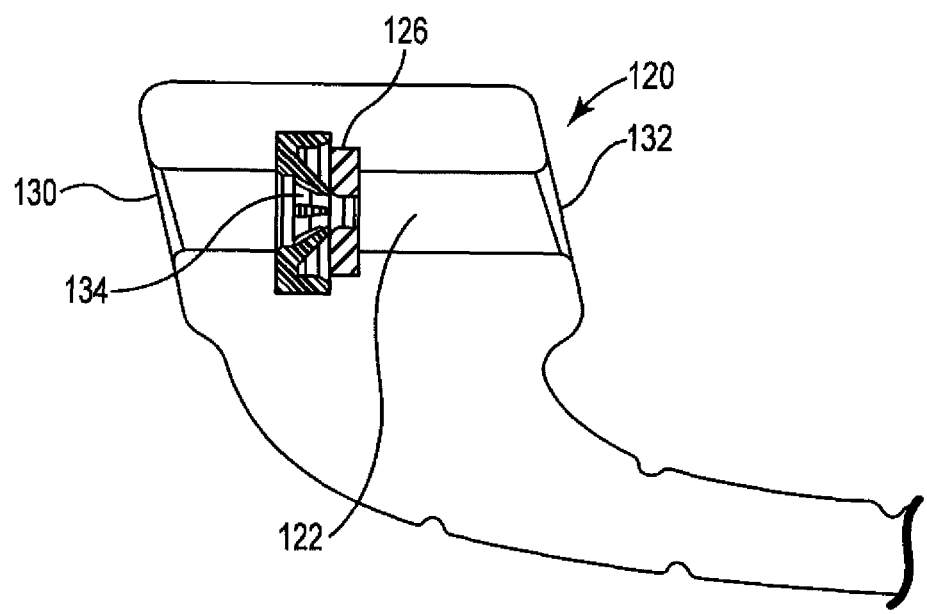
FIG. 7 is a cross-sectional view of the distal end of the tool illustrated in FIG. 4.

As is best illustrated in FIG. 7, gasket 126 is spaced between the open ends 130, 132 of the central opening 122 and is adjacent to an optional locking eyelet system 134. Locking eyelet system 134 includes multiple prongs that can are designed for engagement with the surface of the extension portion when it is positioned within the central opening 122. In use, an elongate portion of an implant (e.g., mesh or a polymeric rod of an extension portion piece) may be threaded through the central opening 122, including the eyelet system 134. The housing around the eyelet system 134 further blocks tissues from contacting the eyelet/mesh interface, which prevents interference with tissue. The gasket 126 also prevents or minimizes entanglement between mesh and the locking eyelet prongs as the mesh moves through the tool, as this gasket is positioned adjacent to the free ends of the prongs that could otherwise engage with mesh material.

Figure 8A:
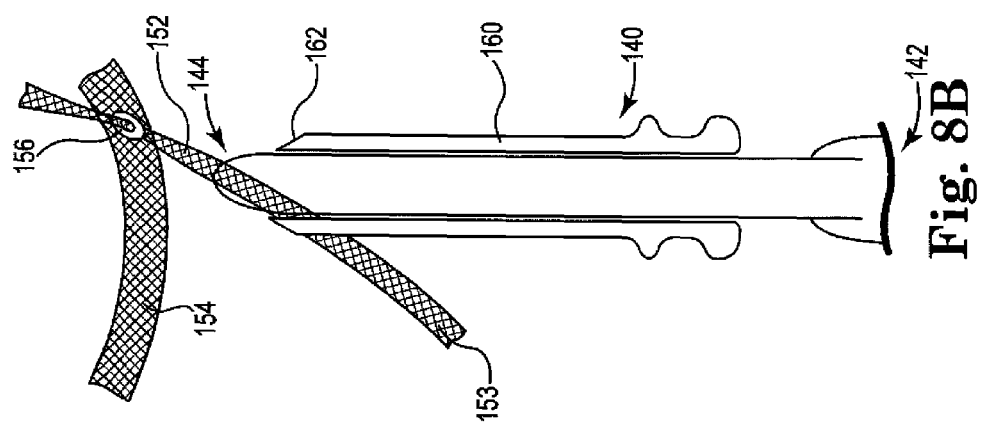
FIGS. 8A and 8B are schematic cross-sectional front views of an exemplary embodiment of an adjusting and cutting tool of the invention as positioned relative to an implant.
Figure 8B:
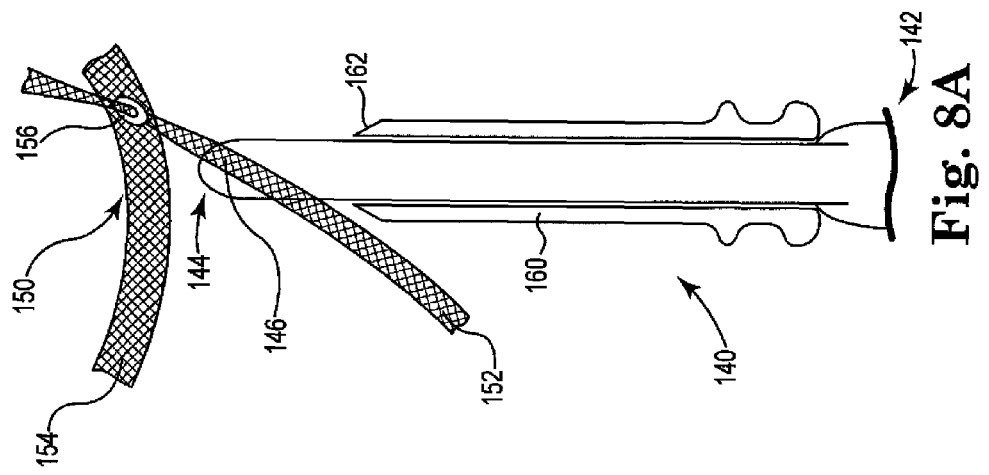

FIGS. 8A and 8B illustrate an implant, tool, and method related to providing support for urethral tissue by retropubic fixation and support of a multi-piece implant. The implant can be placed by an adjusting and cutting tool 140, such as can be accomplished transvaginally and retropubically. The tool 140 includes a proximal end 142 and a distal end 144. A channel or aperture 146 extends through the tool 140 generally adjacent to its distal end 144, which channel 146 is sized so that a portion of an implant can be fed through it. In particular, the distal end 144 of tool 140 is engageable with a portion of a first piece 152 of a multi-piece implant 150 in a manner that allows the tool 140 to be "pushed" or otherwise manipulated to adjust the size (length) of the implant 150 at a frictional adjusting engagement. In this exemplary embodiment, the implant 150 further includes a second piece 154 that is adjustably attached to the first piece 152 at an adjustment area, such as at the frictional grommet 156 shown in the figures.

The tool 140 also includes a cutting mechanism 160 that includes a distal cutting blade 162. In operation, after the tool 140 is used to adjust the implant 150 (e.g., adjustment of the overall implant 150 within the patient and/or adjustment of the first and second pieces 152, 154 relative to each other), the cutting mechanism 160 can be translated or slid toward the distal end 144 of the tool 140 to sever a portion 153 of the first piece 152 of the implant 150 that extends past the cutting mechanism 160. The length of the channel 146 can be selected to provide a predetermined fixed length of the first implant piece 152 after it is severed. The cutting mechanism 160, as illustrated, can be configured as a tube that includes a continuous or multiple cutting surfaces at its distal end. Movement of an actuator at the proximal end can actuate the cutting mechanism 160. In one example, an actuator can be manipulated to cause a sliding movement of the cutting mechanism relative to the distal end 144 of the tool 140 in order to cause the cutting mechanism (blades) to sever a portion of implant that is held at the distal end (i.e., adjacent to the portion of the implant extending through the channel).

Figure 9B:
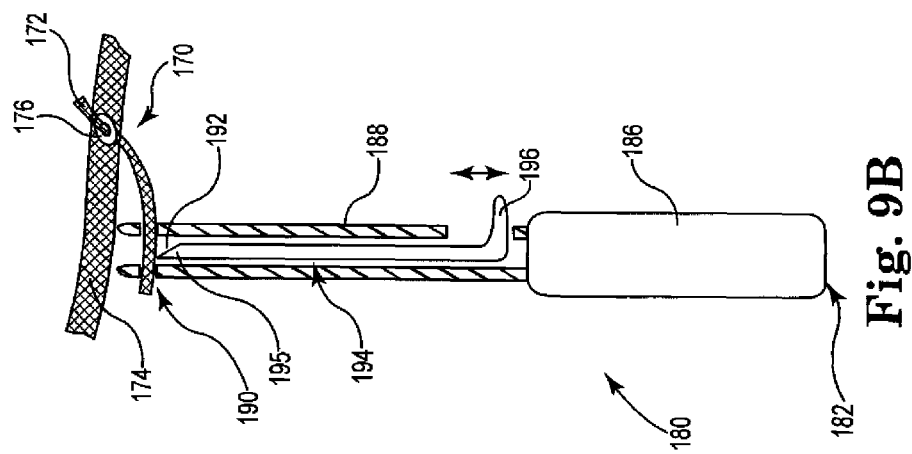
FIGS. 9A and 9B are a front view and a side cross-sectional view, respectively, of an exemplary embodiment of an adjusting and cutting tool of the invention, as positioned relative to an implant.
Figure 9A:
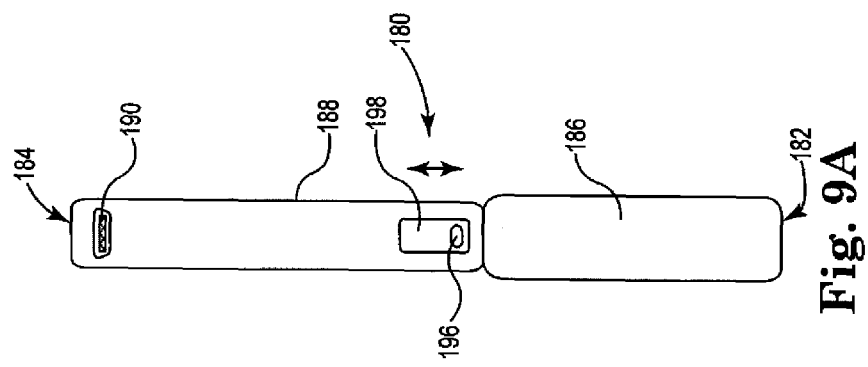

FIGS. 9A and 9B illustrate another exemplary tool and implant useful for providing support for urethral tissue by retropubic fixation and support of a multi-piece implant, such as can be accomplished transvaginally and retropubically. In this embodiment, a multi-piece implant 170 includes a first piece 172 and a second piece 174 that are adjustably attached to each other at an adjustment area, such as at the frictional grommet 176 shown in the figures. A tool 180 is used for both adjustment and cutting of the implant 170, and includes a proximal end 182, a distal end 184, a handle 186 at the proximal end 182, and a shaft 188 extending distally from the handle 186. The shaft 188 includes a first aperture 190 adjacent to the distal end 184 through which a first piece 172 of the implant 170 can be threaded. The shaft 188 further includes an internal channel 192 in which a cutting mechanism 194 is positioned. Cutting mechanism 194 includes one or more cutting surfaces or blades 195 at its distal end and an actuation lever 196 at its proximal end.

The shaft 188 further includes a second aperture 198 through which the actuation lever 196 can extend. The actuation lever 196 is moveable relative to the length of the shaft 188 so that it can cut the material of the implant 170 in a desired location after positioning and adjustment of the first and second pieces 172, 174 of the implant 170 is complete. Movement of the cutting mechanism 194 of the tool 180, such as by manual actuation or with another tool or device, will move the cutting mechanism 194 so that blades 195 can sever the implant. In one example, an actuator, such as the actuation lever 196, can be manipulated to cause a sliding or translational movement of the cutting mechanism 194 toward the distal end 184 of the shaft 188 in order to cause the cutting surfaces or blade 195 to sever a portion of implant that is held at the distal end (i.e., adjacent to the portion of the implant extending through the first aperture 190). Although the shaft 188 is shown as being somewhat oblong in shape, it is understood that it can instead have a different cross-sectional shape, such as square, rectangular, circular, or another shape, which may be tapered or have a constant cross-section along its length.

In accordance with the above embodiments and/or other embodiments of the invention described and illustrated herein, blades or similar cutting mechanisms may be replaced or supplemented with other cutting surfaces or devices, such as a sharp wire or multiple sharp wires. In addition, such wires may optionally be connected to a power source so that they are heated to a temperature that is sufficient to cut through a mesh or other implant material. Such wires can be pulled or pushed through implant material held by a shaft at a distal end, for example. Such wires can be located at a distal end, near implant material held by a shaft, and can be moved by an actuator at a proximal end, for example.

FIGS. 10A and 10B illustrate another embodiment of an adjusting and cutting tool 200. Tool 200 includes a proximal end 202, a distal end 204, and an integrated cutting mechanism 206 that can be actuated at the proximal end 202 to cut an implant material at the distal end 204. The tool 200 further includes an elongated shaft member 208 from which an angled member 210 extends. Angled member 210 includes an aperture 212 through which an elongate portion of implant material (e.g., mesh) can be threaded, and in which the implant material can be severed by actuation of the cutting mechanism or blade 206. The shaft member 208 includes a central channel 216 in which an actuation member 218 extends, which actuation member may be a flat ribbon or other elongated structure, for example. The actuation member 218 may be functionally attached at its distal end to the cutting mechanism 206 and at its proximal end to a blade actuator 220. In this example, the actuator 220 is a button that extends upwardly from a top surface of the shaft member 208 and that is slideable, such as along the length of a slot 222 of the shaft member 208. In this way, the actuator 220 can be manipulated by sliding it in a distal direction to cause the cutting mechanism or blade 206 to sever a portion of implant that is held at the distal end through the aperture 212.

The angled member 210 can be positioned or angled relative to the shaft 208 to expose a desired distal surface 224 in a distal direction. That distal surface, which is adjacent to the aperture on a distal side of the aperture, may be useful as an adjusting surface to contact a piece, component, or other structure of an implant and place pressure, to push that piece, component, or other structure in a distal direction relative to an elongate piece of implant that is threaded through the aperture.

Figure 11:
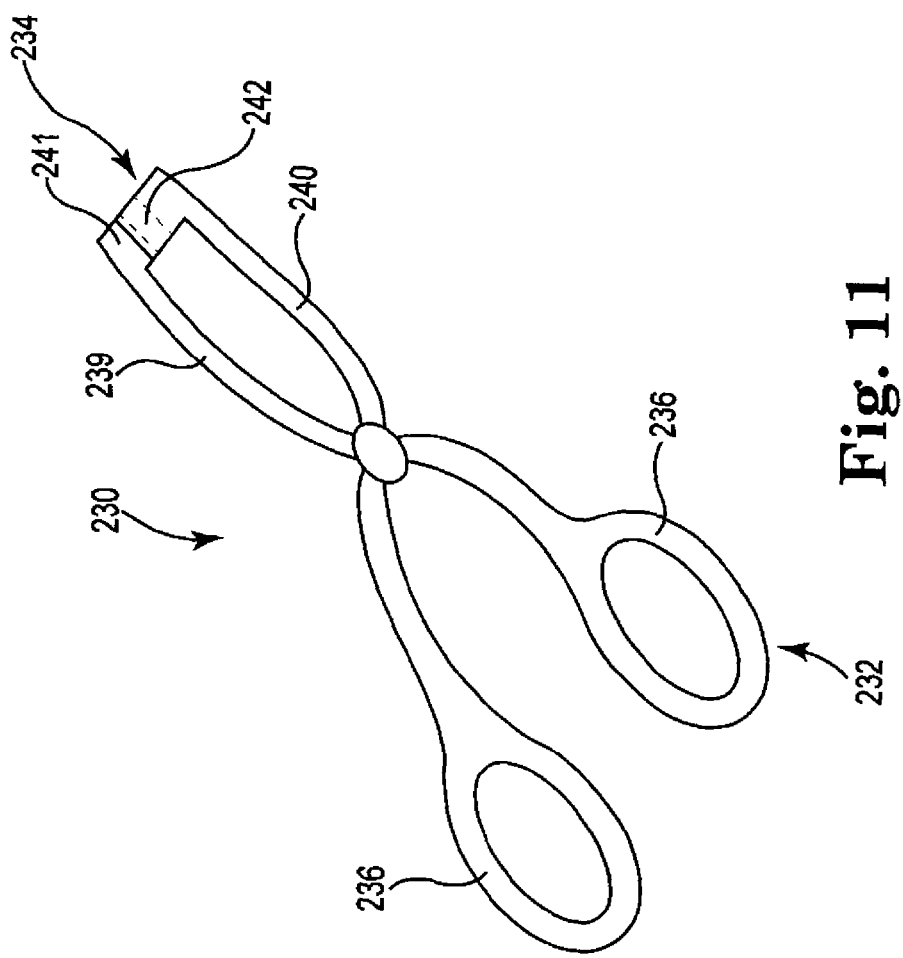
FIG. 11 is a perspective view of an exemplary embodiment of an adjusting and cutting tool of the invention.

FIG. 11 illustrates another embodiment of a tool 230 useful for placing, adjusting, and cutting an implant that is positioned within a patient. Tool 230 includes a proximal end 232, a distal end 234, and an integrated cutting mechanism at the distal end 234. Tool 230 can be actuated at the proximal end 232 to cut implant material that is positioned at the distal end 234. The tool 230 is generally configured similar to a pair of scissors, and includes handles or grips 236 at its proximal end that can be manipulated to control the structure at the distal end 234. The distal end 234 includes two arms 239, 240 that are moveable toward and away from each other through corresponding movements of the handles 236. The distal end of arm 239 includes a cutting blade or member 241, and the distal end of arm 240 includes a structure through which a channel 242 extends. Channel 242 is sized and positioned to accept a portion of an implant material, such as mesh. The distal end 234 can be engaged with a portion of implant material, such as by threading it through the channel 242, and then the cutting blade or member 241 can be actuated to contact the implant material and sever the material held at the channel 242.

Figure 12:
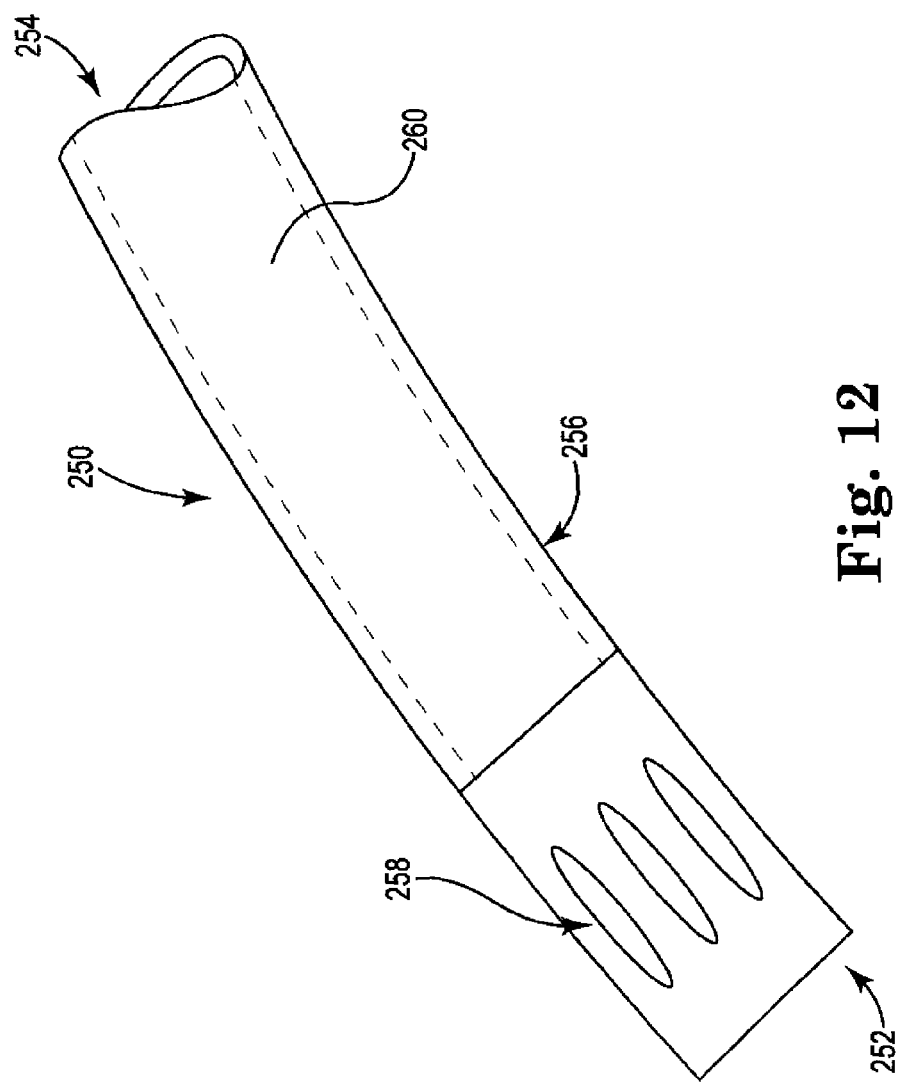
FIG. 12 is a perspective view of an exemplary embodiment of an adjusting and cutting tool of the invention.

FIG. 12 illustrates another embodiment of a tool 250 useful for placing, adjusting, and cutting an implant that is positioned within a patient. Tool 250 includes a proximal end 252, a distal end 254, and an integrated cutting mechanism (e.g., blades) that can be actuated at the proximal end 252 to cut an implant material at the distal end 254. Tool 250 further includes a handle portion 258 at its proximal end 252 and an elongate shaft 256 extending distally from handle portion 258. An elongate interior channel 260 extends through the length of elongate shaft 256. The channel 260 is capable of containing a portion of an implant, such as an elongate piece of implant material, and the shaft 256 also includes a cutting mechanism (not visible) located internally within the channel 260. The cutting mechanism can include one or more sharp blades or other cutting surfaces that can be actuated by movement of an actuator at the proximal end 252, such as by twisting or rotating the handle portion 258 relative to the shaft 256. This twisting or rotating motion will sever a portion of implant that is held within the internal channel 260 of the elongate shaft.

Figure 13:
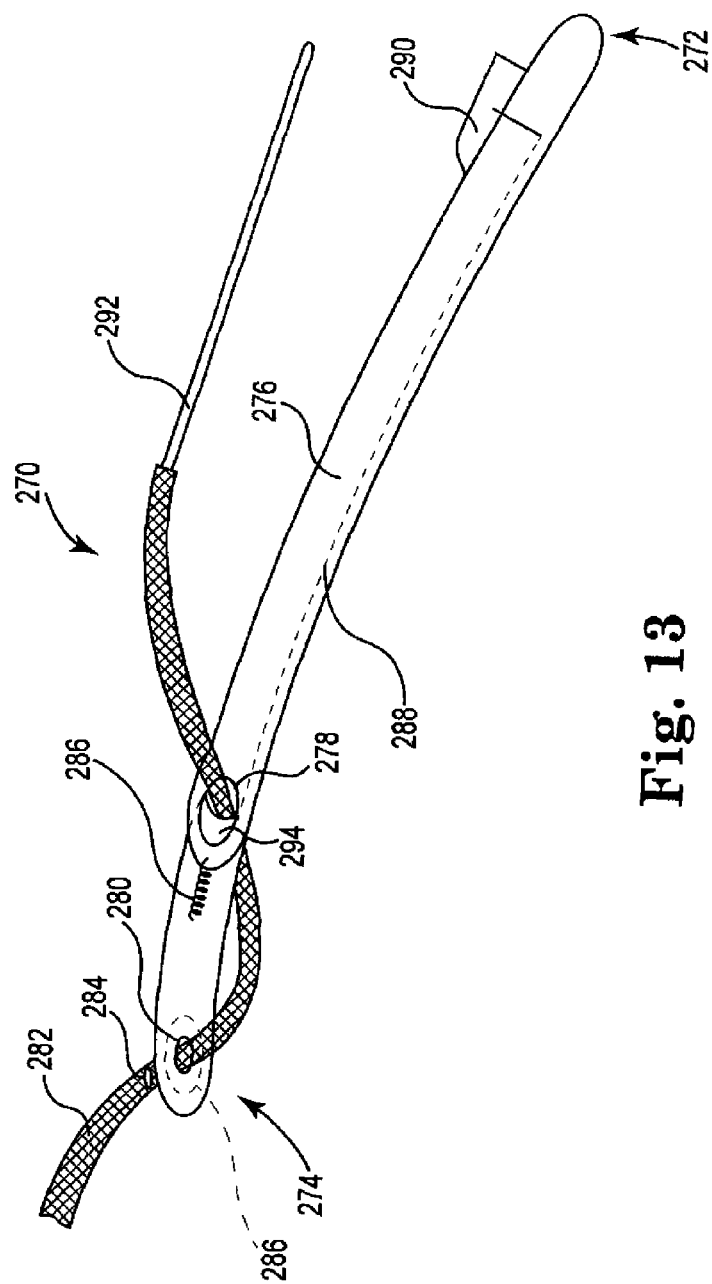
FIG. 13 is a perspective view of an exemplary embodiment of an adjusting and cutting tool of the invention, as positioned relative to an implant.

FIG. 13 illustrates another embodiment of a tool 270 useful for placing, adjusting, and cutting an implant that is positioned within a patient. Tool 270 includes a proximal end 272, a distal end 274, and an integrated cutting mechanism (e.g., blades) that can be actuated at the proximal end 272 to cut an implant material at the distal end 274. Tool 270 includes an elongate shaft 276 that includes a first aperture 278 spaced from a second aperture 280, both of which are located proximal to the distal end 274. The apertures 278, 280 are sized and spaced to allow an elongate portion of an implant, such as the illustrated implant portion 282, to be threaded through them. The implant portion 282 can be provided with a rod arm 292 (e.g., a polymeric rod arm) at one of its ends, which can facilitate threading of the implant through the apertures 278, 280.

The first aperture 278, which is proximal to the second aperture 280, is capable of containing a portion of an implant in a location so that it can be cut by the cutting mechanism. The first aperture 278 further includes a blade or other cutting mechanism 294 that can be actuated by movement of an actuator at the proximal end, such as by sliding the actuator relative to the length of the shaft 276, to sever a portion of implant where it is held within the first aperture 278. In one exemplary embodiment, elongate shaft 276 includes a cable or wire 288 extending along or within a portion of its length that is functionally engaged with a blade actuator 290 and the cutting mechanism 294 such that movement of the actuator 290 will cause the cutting mechanism 294 to cut the implant material. The cutting mechanism 294 may also be functionally engaged with a spring 286 that can be used to bias the cutting mechanism 294 between its cutting and neutral positions.

Also at the distal end is a surface adjacent (an adjusting surface) to a second (distal) aperture that is capable of engaging a grommet 284 that is engaged with an elongate portion of implant that is threaded through the distal aperture. The adjusting surface has a flat area that corresponds to a flat surface of the grommet, such that the adjusting surface can be used to push the grommet distally along a length of elongate implant piece, by manipulating the proximal end (holding the proximal end and moving the proximal end in a distal direction).

Figure 14:
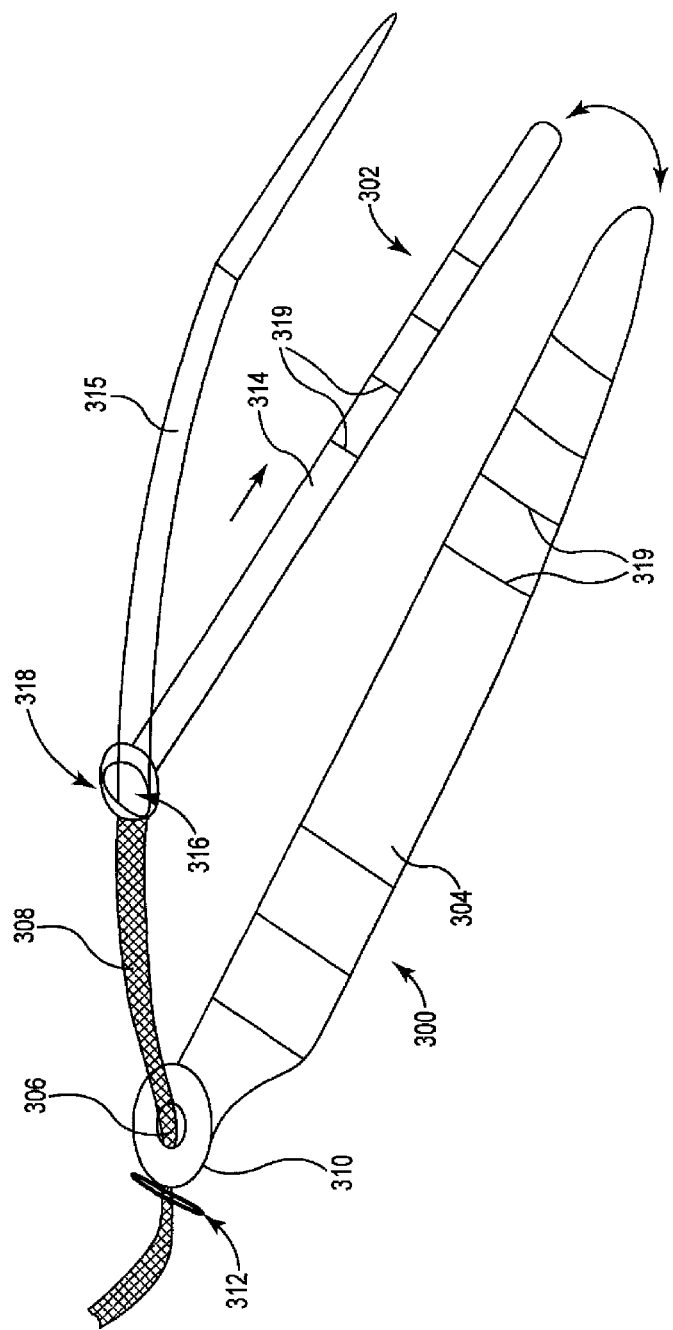
FIG. 14 is a perspective view of an exemplary embodiment of an adjusting and cutting tool of the invention, as positioned relative to an implant.

FIG. 14 illustrates an alternate set of tools useful for placing, adjusting, and cutting an implant positioned within a patient. The set of tools includes an adjusting tool (or a "guide tool") 300 and a cutting tool 302. Each tool has a proximal end and a distal end. The adjusting tool 300 includes an elongate shaft 304 with an aperture or opening 306 at its distal end, through which an elongate portion of an implant 308 may be threaded. The aperture 306 is capable of engaging a portion of the implant 308 at a location that enables the cutting tool 302 to sever it at a desired location. Adjacent to the aperture 306 is an adjusting surface 310, which may be configured as a flat area that corresponds to a flat surface of a grommet 312. In this way, the adjusting surface 310 can be used to push the grommet 312 distally along a length of the elongate implant piece 308, by manipulating the proximal end (e.g., holding the proximal end and moving it in a distal direction).

The cutting tool 302 includes an elongate shaft 314 and an aperture 316 at its distal end. The distal end of the cutting tool 302 also includes a blade 318 or other cutting mechanism that can be manipulated to sever the implant material. For example, the blade, or an actuation mechanism that is functionally connected to the blade, can be pulled or moved proximally to sever the implant material. In order to maintain the various components in their desired positions, it may be useful to provide the implant piece 308 with a rod arm 315 that can be held in position or otherwise manipulated while the cutting tool 302 is pulled in a proximal direction so that its cutting mechanism or blade 318 will sever the elongate implant piece 308. Optionally, the cutting tool 302 may include an actuator at the proximal end that can be moved to cause the blade 318 to sever the implant material held at the aperture.

Demarcations or indicia 319 can optionally be provided on a surface of the shaft 314 of the cutter tool 302, such as generally at its proximal end, and/or corresponding demarcations or indicia 319 can be provided generally at the proximal end of the adjusting tool 300. The indicia 319 can be used as external markings that are visible to the user and are therefore useful to gauge the distance between the distal end blade 318 of the cutting tool 302 and the distal end (e.g., aperture) of the adjusting tool 300.

Figure 15B:
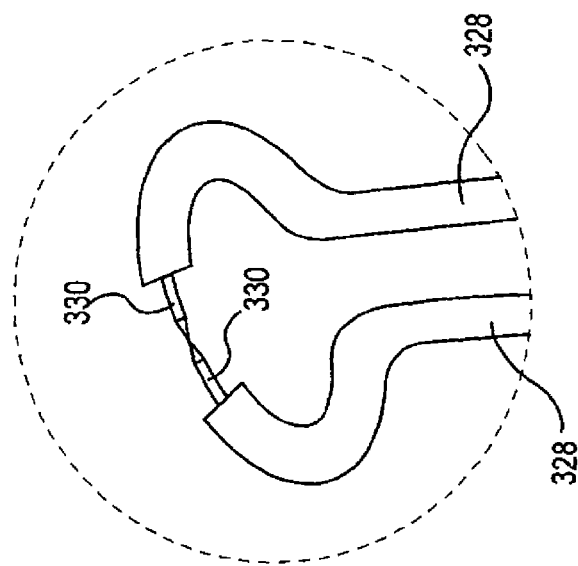
FIG. 15B is an enlarged view of a distal end of the tool illustrated in FIG. 15A.
Figure 15A:
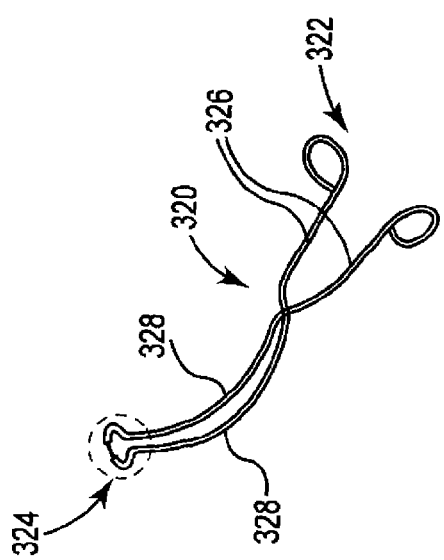
FIG. 15A is a perspective view of an exemplary embodiment of an adjusting and cutting tool of the invention.

FIGS. 15A and 15B illustrate another embodiment of a tool 320 useful for placing, adjusting, and cutting an implant that is positioned within a patient. Tool 320 includes a proximal end 322, a distal end 324, and an integrated cutting mechanism at the distal end 324. Tool 320 can be actuated at the proximal end 322 to cut implant material that is positioned at the distal end 324. The tool 320 is generally configured similar to a pair of scissors or forceps (e.g., Allis Babcock forceps), and includes handles or grips 326 at its proximal end that can be manipulated to control the structure at the distal end 324. The distal end 324 includes two arms 328 that are curved in order to allow for additional procedures to take place during the cutting operation. In other words, the curve of these arms 328 can match the curve of a needle to provide easier access to a target area. The arms 328 are moveable toward and away from each other through corresponding movements of the handles 326.

The distal end of both of the arms 328 includes a cutting blade or member 330, as is best shown in the enlarged view of the distal end 324 of the tool 320 (see FIG. 15B). The cutting blade or members 330 can be moved toward each other and a portion of an implant material that is positioned where the cutting blades or members 330 will contact each other. When the members 330 are sufficiently close to each other, the implant material between them will be severed.

Tool 320 may further include a ring or other guide that can move along the length of the implant, which allows the end to be closed when inserting the material. Once the implant is in its desired position, the arms 328 can be squeezed together at their distal ends to cut the mesh. In other words, the tool 320 can engage the guide to be led from an external location, along a length of the implant, to a location of the implant that is desired to be severed. Once at that location, the distal end of the tool can be opened, placed to contact the implant material, then closed to sever the implant material.

FIGS. 16A and 16B illustrate a distal end 342 of another embodiment of an adjusting and cutting tool 340. Tool 340 includes an integrated cutting mechanism or blade 344 that can be actuated at a proximal end (not shown) of tool 340 to cut an implant material at the distal end 342. The tool 340 further includes an elongated shaft member 346 from which an angled member 348 extends. Angled member 348 includes an aperture 350 through which an elongate portion of implant material (e.g., mesh) can be threaded, and in which the implant material can be severed by actuation of the cutting mechanism or blade 344.

As illustrated, the cutting mechanism 344 may include a curved or semi-circular blade member having an inner cutting edge 345 that is sufficiently sharp to cut a mesh or implant material that is inserted into the aperture 350 and adjusted until the area that is to be severed is positioned adjacent to the cutting edge 345. It is understood that the cutting mechanism may instead have a different shape than a semi-circle, wherein the cutting edge 345 is configured to sever the implant material. The distal end 342 may further include a recess 356 (see FIG. 16B) which provides clearance for the cutting mechanism as it moves from one side of the aperture 350 to its other side to allow the cutting blade to move across the entire diameter of the aperture 350, if desired.

In order to actuate the cutting mechanism or blade 344, one or more actuation wires or other elongated structures 352 are operatively attached to one or more locations of the blade 344, wherein such wires can extend within or along at least a portion of the length of shaft member 346. The structure(s) or wire(s) 352 may be functionally attached at their distal ends to the cutting mechanism or blade 344. In this example, the wires 352 can be pulled or actuated at their distal ends to pull the cutting mechanism 344 in a proximal direction so that it passes over the aperture 350 and severs the portion of implant that is held at the distal end through the aperture. Moving the cutting blade 344 in this manner can either be accomplished through manual actuation of the wires 352 or with the use of some other type of actuation mechanism.

Figure 17:
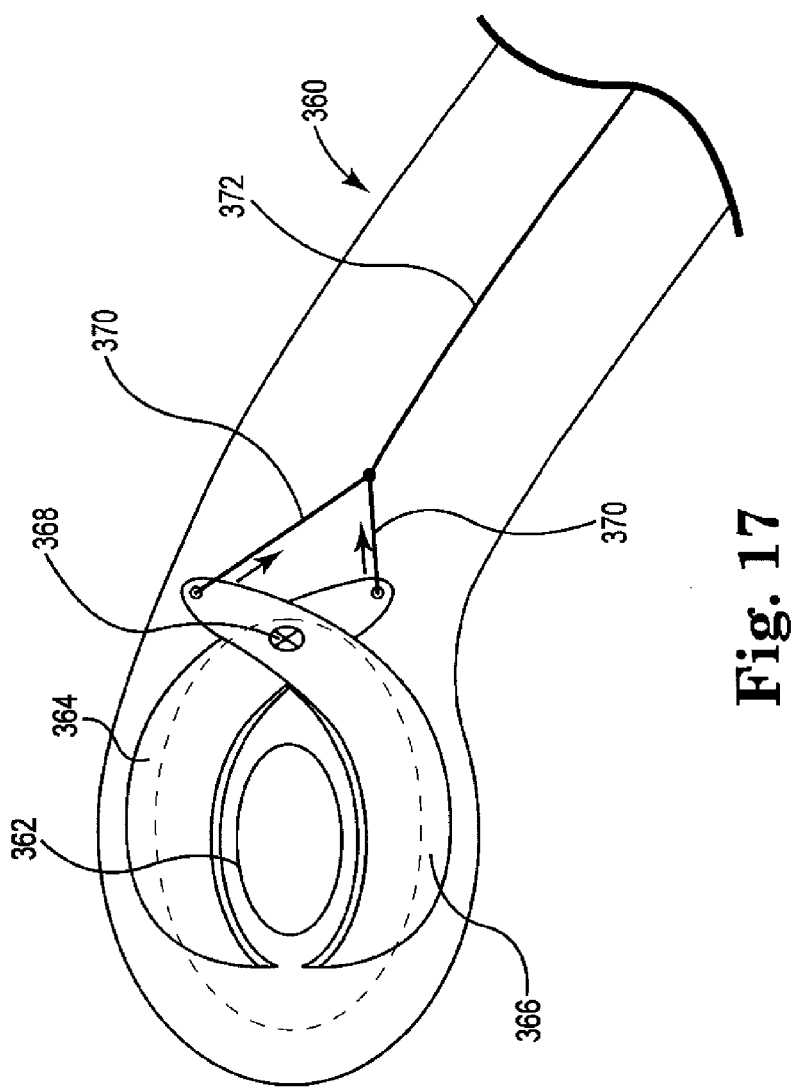
FIG. 17 is a top view of an exemplary embodiment of an adjusting and cutting tool of the invention.

FIG. 17 illustrates a distal end of an adjusting and cutting tool 360 that is similar to the tool 340 illustrated in FIGS. 16A and 16B, but tool 360 includes a different configuration of a cutting mechanism. In particular, the cutting mechanism of tool 360 includes a first curved blade 364 and a second curved blade 366 that are rotatably attached to each other at pivot point 368 so that they are adjacent to an aperture 362. Each of the blades 364, 366 includes a proximal portion that extends beyond the pivot point 368 (i.e., on the opposite side of the pivot point 368 from the portion of the blades 364, 366 that will be used to sever material within the aperture) and to which an actuation wire 370 is attached. The actuation wires 370 of the two blades 364, 366 may optionally be connected to each other at another extension wire 372, as shown, to allow for pulling or actuation of a single wire 372 to cause the blades 364, 366 to pivot about a single point and move toward each other in a scissor-type motion to traverse the aperture 362 and sever a mesh material held within the aperture. Alternatively, the wires 370 can be pulled individually or pulled toward each other and pulled together as a unitary actuator.

Figure 18:
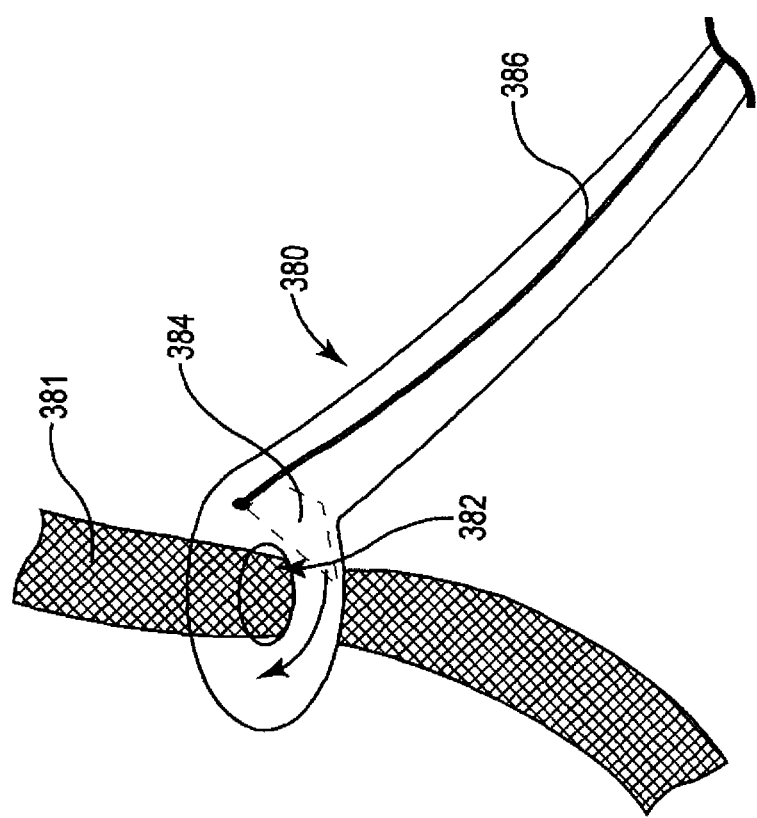
FIG. 18 is a perspective view of an exemplary embodiment of an adjusting and cutting tool of the invention, as positioned relative to an implant.

FIG. 18 illustrates a distal end of an adjusting and cutting tool 380 that is similar to the tool 340 illustrated in FIGS. 16A and 16B, but tool 380 includes a different configuration of a cutting mechanism 384. In particular, the cutting mechanism 384 of tool 380 includes a spinning or rotating cutting blade that is actuatable to cut an implant material (e.g., an elongated mesh implant material 381 shown in this Figure) that is positioned within an aperture 382 of the tool 380. The cutting mechanism 384 can be actuated by a single wire 386 or other actuation member that allows the spinning or rotation to take place. The cutting mechanism 384 may be provided in layers or located below the aperture 382 so that it does not interfere with the implant material 381 before it is desired to cut that material.

Figure 19A:
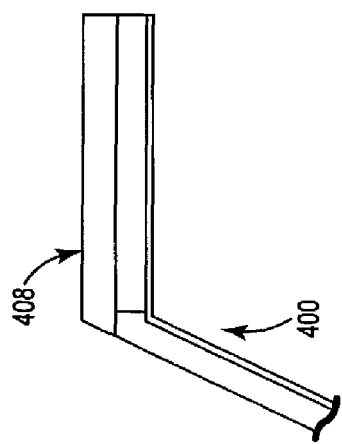
FIGS. 19A and 19B are side and bottom views, respectively, of an exemplary embodiment of an adjusting and cutting tool of the invention.
Figure 19B:
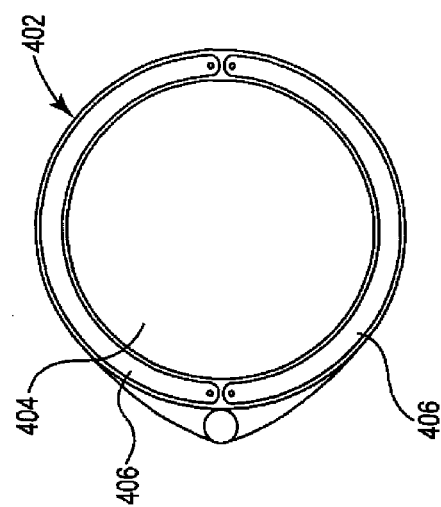

FIGS. 19A and 19B illustrate a distal end of a distal end of an adjusting and cutting tool 400 that is similar to the tool 340 illustrated in FIGS. 16A and 16B, but tool 400 includes a different configuration of a cutting mechanism 402 located adjacent to an aperture 404 of tool 400. In this embodiment, cutting mechanism 402 includes blades 406 that can be actuated via a actuating mechanism that extends along the length of an enlongated shaft of the tool 400, for example. As shown in the bottom view of FIG. 19B, the blades 406 can be configured in such a way that they generally match the size and shape of an adjusting surface 408 of the tool 400. Actuation of the blades 406 will cause them to move across the open area of the aperture 404, thereby severing the implant material that is positioned in the aperture 404.

Figure 20:
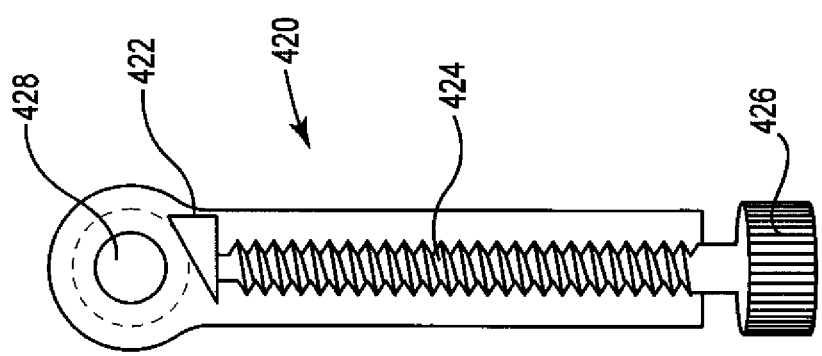
FIG. 20 is a front view of an exemplary embodiment of an adjusting and cutting tool of the invention.
Figure 21:
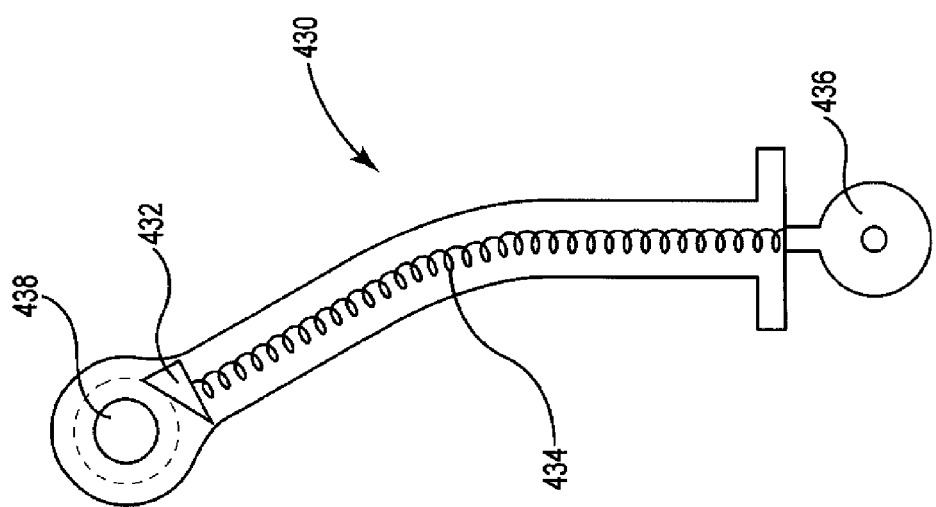
FIG. 21 is a front view of an exemplary embodiment of an adjusting and cutting tool of the invention.

FIGS. 20 and 21 illustrate additional embodiments of adjusting and cutting tools 420 and 430, respectively, which are similar to those described above that include a shaft and a distal angled portion at one end of that shaft that includes an aperture through which implant material can be positioned. With these embodiments, along with many others of the invention, the distal end further includes an adjusting surface that can be used to adjust the positioning of an implant within a patient and/or to adjust multiple pieces of an implant relative to each other.

With particular regard to tool 420 of FIG. 20, a cutting mechanism or blade 422 is provided that is operatively attached to threads 424 that extend proximally through the length of the tool 420. These threads 424 are attached at a proximal end of the device to a screw mechanism 426 that is rotatable to cause movement of the blade 422 across an aperture 428 to thereby sever any implant material extending through it.

With particular regard to tool 430 of FIG. 21, a cutting mechanism or blade 432 is provided that is operatively attached to a compressive spring 434 that extends proximally through at least a portion of the length of the tool 430. Spring 434 is attached at a proximal end of the device to an actuation mechanism 436 that provides for movement of the blade 432 across an aperture 438 to thereby sever any implant material extending through it. That is, the blade 432 can move in a distal direction across the aperture 438 upon application of pressure at the actuation mechanism 436, which can be applied in a distal direction. The pressure or force will translate through the spring 434 to cause the blade 432 to move across the aperture 438.

Figure 22:
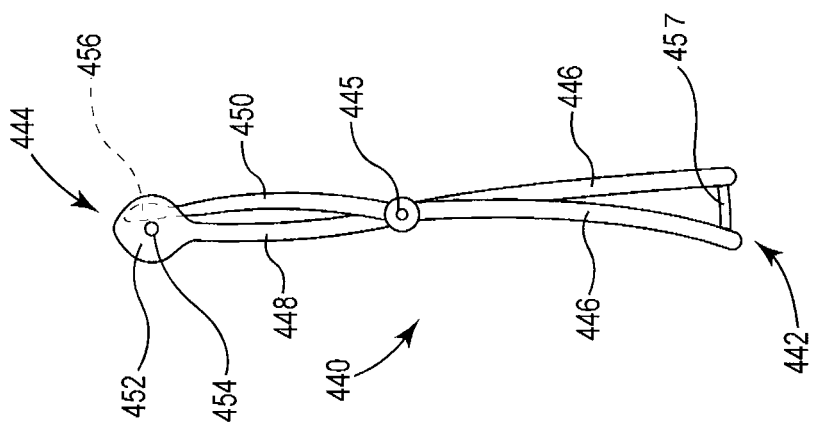
FIG. 22 is a front view of an exemplary embodiment of an adjusting and cutting tool of the invention.

FIG. 22 illustrates another embodiment of a tool 440 useful for placing, adjusting, and cutting an implant that is positioned within a patient. Tool 440 includes a proximal end 442, a distal end 444, and an integrated cutting mechanism at the distal end 444. Tool 440 can be actuated at the proximal end 442 to cut implant material that is positioned at the distal end 444. The tool 440 is generally configured similar to a pair of scissors, and includes members 446 extending proximally from a pivot point 445, which members 446 be manipulated to control the structure at the distal end 444. The tool 440 includes two arms 448, 450 that extend distally from the pivot point 445 and that are moveable toward and away from each other through corresponding movements of the members 446. The distal end of arm 448 includes an adjusting surface 452 and an aperture 454, while the distal end of arm 450 includes a cutting blade 456. When the arms 448, 450 are moved toward each other via movement of the members 446, cutting blade 456 moves across the aperture 454 to sever the implant material that extends through it. In other words, the blade 456 (which may include one or more cutting surfaces) moves in a lateral direction across the aperture upon movement of arms at the proximal end of the tool. Tool 440 may optionally include a safety guard 457 at the proximal end 442, which is configured to prevent movement of the cutting blade 456 relative to the aperture 454 until the guard 457 is removed or reoriented. The guard 457 is illustrated as a single elongated member, but can instead be configured differently to prevent unintentional activation of the cutting mechanism of this tool 440.

Figure 23:
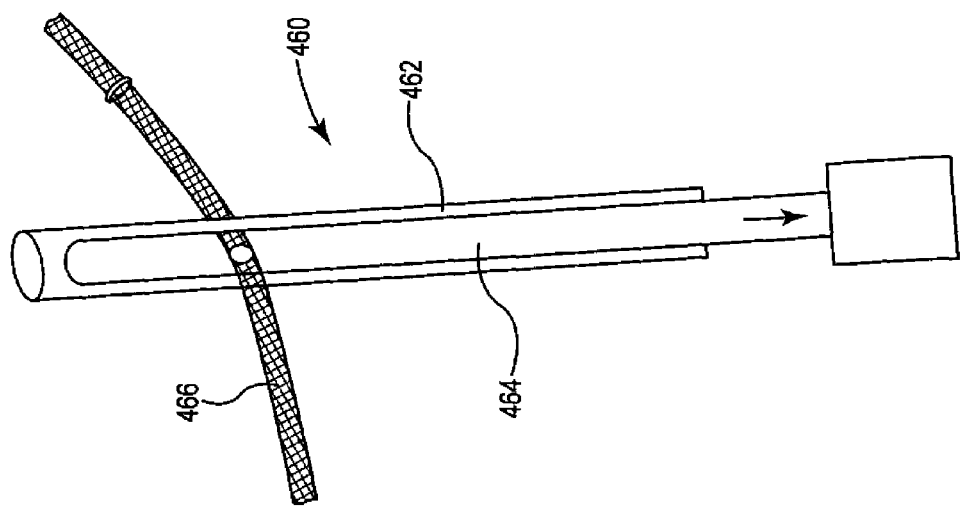
FIG. 23 is a front view of an exemplary embodiment of an adjusting and cutting tool of the invention, as positioned relative to an implant.

FIG. 23 illustrates another embodiment of a tool 460 useful for placing, adjusting, and cutting an implant that is positioned within a patient. Tool 460 includes an inner shaft or tube 464 positioned within an outer tube or shaft 462. An elongate portion of an implant 466 (e.g., mesh) can be threaded through the inner and outer tubes or shafts 462, 464, as shown. The inner and outer shafts can be moved relative to each other, such as by sliding the inner shaft 464 proximally as the outer shaft 462 is held stationary. Upon such relative movement of the portions of the shaft, a cutting mechanism between the two portions will sever the elongate portion of mesh.

Figure 24:
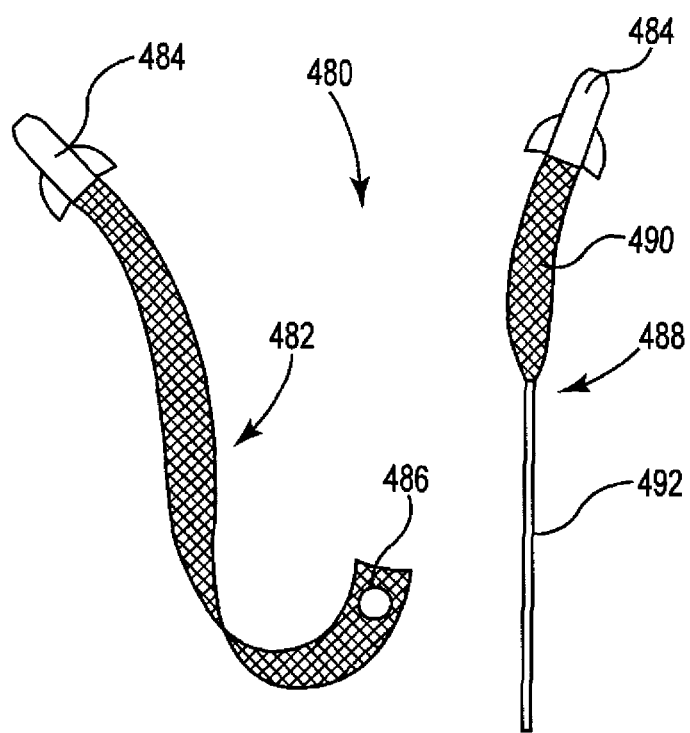
FIG. 24 is an exploded view of two pieces of a multi-piece implant.
Figure 25:
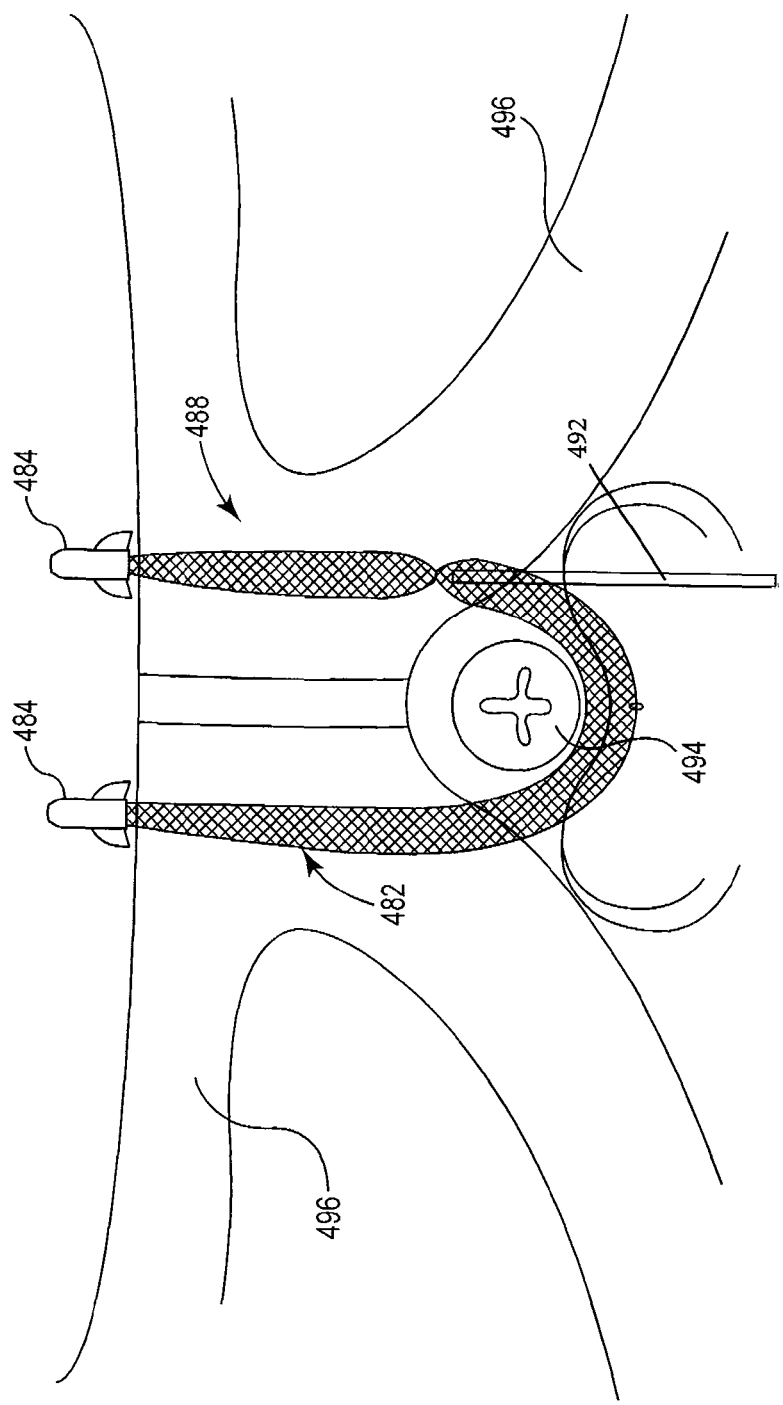
FIG. 25 is a schematic front view of an exemplary positioning of an implant of the type illustrated in FIG. 24 relative to the anatomy of a patient.

An exemplary embodiment of an implant that can be used according to exemplary methods herein is illustrated in FIGS. 24 and 25. FIG. 24 shows a multi-piece implant 480 that can be used for treating urethral incontinence, e.g., stress urinary incontinence in a female patient. The implant 480 includes an elongate extension portion 482 having an anchor 484 at one end and a grommet 486 (e.g., a one-way adjusting frictional grommet) or other attachment feature at an opposite end. The implant 480 further includes a tissue support member 488 that includes a mesh portion 490 from which an anchor 484 extends at one end and from which a rod 492 (e.g., a polymeric rod) extends at an opposite end. The rod 492 can be passed through the grommet 486 or other frictional adjustment feature, and then adjustment of the extension portions 482 and the tissue support member 488 can be performed. The anchors 484 may be soft tissue anchors such as self-fixating tips, for example.

Referring additionally to FIG. 25, each self-fixating tip 484 of implant 480 is shown as being placed in an exemplary location at tissue of a retropubic space, and the tissue support portion is placed below a urethra 494. In exemplary methods, these steps can be performed transvaginally, through a single incision in vaginal tissue, laparoscopically, or surgically. Upon placement of the two self-fixating tips 484 relative to pelvic bone 496, the rod 492 can be passed through the grommet (not visible in this figure). An adjusting and cutting tool, such as one or more of those described herein, can be used to engage the rod or adjacent implant material, and an adjusting surface can be used to adjust the length of the implant by moving the rod through the grommet. After adjustment, the adjusting and cutting tool can be used to cut a portion of excess implant that extends on the proximal side of the grommet, which ill include the rod and an amount of mesh material between the rod and the grommet.

The various systems, apparatus, and methods detailed herein can be used with known implant and repair systems or improvements thereof (e.g., for male and female), features and methods, including those disclosed in U.S. Pat. Nos. 7,500,945, 7,407,480, 7,351,197, 7,347,812, 7,303,525, 7,025,063, 6,691,711, 6,648,921, and 6,612,977, International Patent Publication Nos. WO 2008/057261, WO 2007/097994, WO 2007/149348, WO 2009/017680, and U.S. Patent Publication Nos. 2002/151762, 2010/0174134, 2010/0298630, 2002/0028980, 2006/0069301, and 2002/147382, and International Application number PCT/US10/62577 (filed Dec. 30, 2010). Accordingly, the above-identified disclosures are fully incorporated herein by reference in their entirety.

An implant for placement by use of the described tools, methods, and anchors (e.g., helical anchors, self-fixating tips, or otherwise), and their various components, structures, features, materials and methods may have a number of suitable configurations as shown and described in the previously-incorporated references or as described herein or elsewhere. Various methods and tools for introducing, deploying, anchoring, and manipulating implants to treat incontinence, prolapse, or another pelvic condition, as disclosed in the previously-incorporated references are envisioned for possible adapted use with devices and methods described herein.

An implant for use as described herein can include any structural features useful for a desired treatment, including any desired size, shape, and optional features such as adjustability. Any of these features may be previously known, or described in documents incorporated herein, or as described herein, for any particular implant and method. An implant that includes or is otherwise secured, adjusted, and manipulated as described might be useful to treat any type of pelvic condition in a male or a female patient; as a single and non-limiting example, implants and methods as described be used in a transvaginal sacral colpopexy procedure to provide support to vaginal tissue (e.g. a vaginal cuff), through an implant attached at a region of sacral anatomy such as a sacral ligament (e.g., anterior longitudinal ligament)

The present invention has now been described with reference to several embodiments thereof. The entire disclosure of any patent or patent application identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but is also intended to encompass equivalents of those structures.

The invention claimed is:

1. An adjustment tool for adjusting a length of an elongate portion of a pelvic implant, the tool comprising: a proximal end; a distal end;
   an elongate shaft extending between the proximal and distal ends along a first longitudinal axis; and
   a cylindrical member at the distal end that is engageable with the elongate portion of the implant for manipulation of the elongate portion, wherein the cylindrical member comprises:
   a distal end surface at the distal end of the tool and facing in a distal direction, a proximal end surface at a proximal end of the cylindrical member and spaced from the distal end surface along a length of the cylindrical member, and an aperture extending through the length of the cylindrical member, wherein the proximal end surface faces in a proximal direction that is generally opposite the distal direction that the distal end surface faces; and
   a second longitudinal axis extending along the length of the cylindrical member, wherein the second longitudinal axis is generally parallel to the first longitudinal axis and offset along the second longitudinal axis length by a fixed distance from the first longitudinal axis of the elongate shaft;
   wherein the cylindrical member further comprises a gasket positioned within the aperture; and
   wherein the cylindrical member further comprises a locking eyelet system within the aperture and adjacent to the gasket.

2. The adjustment tool of claim 1, wherein the elongate portion of the implant comprises an elongate mesh or rod of an extension portion piece of an adjustable multi-piece implant.

3. The adjustment tool of claim 1, wherein the locking eyelet system comprises multiple prongs that are radially moveable relative to the aperture.

4. The adjustment tool of claim 1, wherein the cylindrical member comprises a slot extending along the length of the cylindrical member, wherein the slot extends between an outer surface of the cylinder and the aperture.

5. The adjustment tool of claim 1, in combination with a multi-piece pelvic implant that comprises an extension portion piece and a support portion piece.

6. The adjustment tool of claim 5, wherein the multi-piece implant comprises an adjusting engagement between an extension portion piece and a support portion piece, and wherein the extension portion piece comprises an anchor at a distal end of the extension portion piece, the anchor comprising one of a helical anchor and a self-fixating tip.

7. The adjustment tool of claim 1, wherein the elongate shaft comprises a curved portion at the distal end of the elongate shaft, wherein the curved portion comprises a distal end that extends directly from an outer curved surface of the cylindrical member.

8. A surgical tool for adjusting and cutting a length of an elongate portion of a pelvic implant, the tool comprising:
   a top surface;
   a bottom surface opposite the top surface;
   a proximal end;
   a distal end engageable with the elongate portion to allow manipulation and cutting of the elongate portion, wherein the distal end comprises:
   an aperture extending from the top surface to the bottom surface and comprising an aperture axis extending through the aperture in a generally perpendicular direction relative to the top and bottom surfaces;
   a recess extending around at least a portion of the aperture; and
   a moveable cutting mechanism having a cutting surface facing toward the proximal end of the tool, wherein the cutting mechanism is at least partially positionable within the recess and moveable from the recess and across a width of the aperture, wherein the recess is sized to enclose at least a portion of the cutting mechanism: and
   an elongate shaft extending between the proximal and distal ends; and
   an actuation mechanism comprising at least one wire comprising a proximal wire end positioned generally at the proximal end of the tool that is operatively attached at a distal wire end to the cutting mechanism for moving the cutting mechanism in a proximal direction across a width of the aperture;
   wherein the cutting mechanism is a semi-circular cutting blade comprising at least one cutting surface.

9. The surgical tool of claim 8, in combination with a multi-piece pelvic implant.

10. The surgical tool of claim 9, wherein the multi-piece implant comprises an adjusting engagement between an extension portion piece and a support portion piece, and wherein the extension portion piece comprises an anchor at a distal end of the extension portion piece, the anchor comprising one of a helical anchor and a self-fixating tip.

11. The surgical tool of claim 8, wherein the actuation mechanism comprises one of a spring and a threaded structure.

12. The surgical tool of claim 8, wherein the cutting mechanism comprises at least two cutting blades that are moveable relative to each other and that are moveable across at least a portion of the width of the aperture.

13. A method of treating vaginal prolapse, the method comprising the steps of:
- providing a multi-piece implant comprising an extension portion piece and a support portion piece, wherein the support portion piece comprises a mesh portion from which an anchor extends at a first end and from which a rod extends at a second end, and wherein the extension portion piece comprises an anchor at first end and a grommet at a second end,
- placing the support portion piece to contact vaginal tissue,
- placing the extension portion piece to contact tissue of a component of sacral anatomy,
- engaging the support portion piece and the extension portion piece at an adjusting engagement by passing the rod through the grommet,
- providing an adjusting and cutting tool comprising:
- a proximal end;
- a distal end engageable with the extension portion piece to allow manipulation and cutting of the extension portion piece, wherein the distal end of the tool comprises an aperture, a recess extending around at least a portion of the aperture, and
- a moveable cutting mechanism having a cutting surface facing toward the proximal end of the tool, wherein the cutting mechanism is at least partially positionable within the recess and moveable from the recess and across a width of the aperture, wherein the recess is sized to enclose at least a portion of the cutting mechanism;
- wherein the cutting mechanism is a semi-circular cutting blade comprising at least one cutting surface,
- an elongate shaft extending between the proximal and distal ends of the tool; and
- an actuation mechanism comprising at least one wire comprising a proximal wire end positioned generally at the proximal end of the tool that is operatively attached at a distal wire end to the cutting mechanism for moving the cutting mechanism in a proximal direction across a width of the aperture;
- using the adjusting and cutting tool to adjust a location of the extension portion piece relative to the support portion piece, and
- using the adjusting and cutting tool to cut the extension portion piece.

14. The method of claim 13, wherein the cutting mechanism is a cutting blade comprising at least one cutting surface.

* * * * *